US011666760B2

(12) United States Patent
Sabesan et al.

(10) Patent No.: US 11,666,760 B2
(45) Date of Patent: Jun. 6, 2023

(54) CRANIAL NERVE STIMULATION TO TREAT SEIZURE DISORDERS

(71) Applicant: LivaNova USA, Inc., Houston, TX (US)

(72) Inventors: Shivkumar Sabesan, Houston, TX (US); Steven E. Maschino, Houston, TX (US)

(73) Assignee: LivaNova USA, Inc., Houston, TX (US)

(*) Notice: Subject to any disclaimer, the term of this patent is extended or adjusted under 35 U.S.C. 154(b) by 130 days.

(21) Appl. No.: 17/216,251

(22) Filed: Mar. 29, 2021

(65) Prior Publication Data

US 2021/0213289 A1 Jul. 15, 2021

Related U.S. Application Data

(63) Continuation of application No. 16/184,789, filed on Nov. 8, 2018, now abandoned, which is a continuation of application No. 14/316,258, filed on Jun. 26, 2014, now Pat. No. 10,124,169.

(60) Provisional application No. 61/840,461, filed on Jun. 28, 2013, provisional application No. 61/888,303, filed on Oct. 8, 2013.

(51) Int. Cl.
*A61N 1/36* (2006.01)

(52) U.S. Cl.
CPC ..... *A61N 1/36064* (2013.01); *A61N 1/36053* (2013.01); *A61N 1/36139* (2013.01); *A61N 1/36178* (2013.01)

(58) Field of Classification Search
CPC ............ A61N 1/36064; A61N 1/36053; A61N 1/36139; A61N 1/36178
See application file for complete search history.

(56) References Cited

U.S. PATENT DOCUMENTS

| | | | |
|---|---|---|---|
| 6,366,813 B1 | 4/2002 | Dilorenzo | |
| 6,473,644 B1 | 10/2002 | Terry et al. | |
| 6,622,041 B2 | 9/2003 | Terry, Jr. et al. | |
| 7,974,696 B1 | 7/2011 | Dilorenzo | |
| 8,382,667 B2 | 2/2013 | Osorio | |
| 8,615,309 B2 | 12/2013 | Craig | |
| 10,124,169 B2 | 11/2018 | Sabesan et al. | |
| 2007/0233193 A1* | 10/2007 | Craig | A61N 1/36082 607/45 |
| 2010/0191304 A1 | 7/2010 | Scott | |
| 2014/0277255 A1* | 9/2014 | Sabesan | A61N 1/36139 607/45 |

OTHER PUBLICATIONS

Grigg-Damberger et al., "Sleep-Related Epilepsy and Electroencephalography", Sleep Medicine, Mar. 2012, vol. 7, No. 1, pp. 46-48 (Year: 2012).*

* cited by examiner

*Primary Examiner* — Catherine M Voorhees
*Assistant Examiner* — Roland Dinga
(74) *Attorney, Agent, or Firm* — Foley & Lardner LLP

(57) ABSTRACT

A method includes applying, by an implantable medical device (IMD), stimulation to a cranial nerve of a patient responsive to a determination that a level of synchrony between neural activity of one or more regions of an autonomic nervous system of the patient and one or more regions of a central nervous system of the patient falls below a first threshold and discontinuing the application of stimulation by the IMD when the level of synchrony exceeds a second threshold.

20 Claims, 24 Drawing Sheets

CRANIAL NERVE STIMULATION TO TREAT SEIZURE DISORDERS

RELATED APPLICATIONS

This application is a continuation of U.S. application Ser. No. 16/184,789, filed Nov. 8, 2018, which is a continuation of U.S. application Ser. No. 14/316,258, filed Jun. 26, 2014, which claims priority to U.S. Provisional Application No. 61/840,461, filed Jun. 28, 2013, and U.S. Provisional Application No. 61/888,303, filed Oct. 8, 2013, all of which are incorporated herein by reference in their entirety.

FIELD OF THE DISCLOSURE

The present disclosure is generally related to cranial nerve stimulation to treat seizure disorders.

BACKGROUND

Seizures may be treated using cranial nerve stimulation (CNS). CNS includes application of an electrical stimulation signal to a cranial nerve, e.g., vagus nerve, of a patient. When the cranial nerve is a vagus nerve, CNS is referred to as vagus nerve stimulation (VNS).

When used to treat seizure disorders, conventional VNS attempts to decrease synchronization of a patient's interconnected cortical regions and/or reduces the duration, spatial spread or severity of seizures. VNS in the treatment of seizure disorders typically uses a pattern of charge-balanced constant current stimulation at stimulus frequencies of 20-30 Hz. Although VNS has proven to be an effective adjunctive treatment for refractory epilepsy, some patients do not respond to the conventional paradigm of VNS therapy or become unresponsive to the therapy over time.

SUMMARY

Application of CNS employing microburst signals may produce a change in synchrony between neural activity of one or more regions of a patient's autonomic nervous system (e.g., the nucleus tractus solitarii (NTS) or other centers responsible for autonomic function regulation) and one or more regions of the patient's central nervous system (e.g., the thalamus and the cortex). Changing synchrony between one or more regions of a patient's autonomic nervous system and one or more regions of the patient's central nervous system may have implications in treatment of epileptic seizures. Systems and methods described herein may provide an improved epileptic seizure treatment.

For example, an implantable medical device (IMD) may determine a measurement indicative of a synchrony between one or more regions of a patient's autonomic nervous system and one or more regions of a central nervous system of the patient. Based on the measurement, the IMD may change the synchrony by applying one or more stimulation signals to a cranial nerve of the patient. The IMD may also adjust one or more stimulation parameters and/or change treatment modalities (e.g., microburst stimulation mode or non-microburst stimulation mode) based on a measurement of synchrony between neural activity of one or more regions of the patient's autonomic nervous system and one or more regions of the patient's central nervous system. CNS may include VNS, trigeminal nerve stimulation (TNS), or stimulation of another cranial nerve, and the one or more stimulation signals may be applied directly or indirectly (e.g., transcutaneously).

In a particular embodiment, a method includes determining a first measurement indicative of a synchrony between neural activity of one or more regions of a patient's autonomic nervous system and one or more regions of the patient's central nervous system. The method also includes changing the synchrony between the neural activity by applying one or more stimulation signals to a cranial nerve of the patient based on the first measurement.

In a particular embodiment, a method includes determining a measurement indicative of a synchrony between neural activity of one or more regions of a patient's autonomic nervous system and one or more regions of the patient's central nervous system. The method also includes changing a stimulation mode (e.g., from non-micro burst stimulation mode to micro burst stimulation mode) based on the measurement.

In a particular embodiment, a device includes a processor configured to determine a first measurement indicative of a synchrony between neural activity of one or more regions of a patient's autonomic nervous system and one or more regions of the patient's central nervous system. The device further includes a therapy delivery unit electronically associated with the processor and configured to apply one or more stimulation signals to a cranial nerve of the patient based on the first measurement.

In a particular embodiment, a device includes a processor configured to determine a measurement indicative of a synchrony between neural activity of one or more regions of a patient's autonomic nervous system and one or more regions of a central nervous system of the patient. The device further includes a therapy delivery unit electronically associated with the processor, where the processor is adapted to change a stimulation mode of the therapy delivery unit based on the measurement.

DETAILED DESCRIPTION

Figure 1:
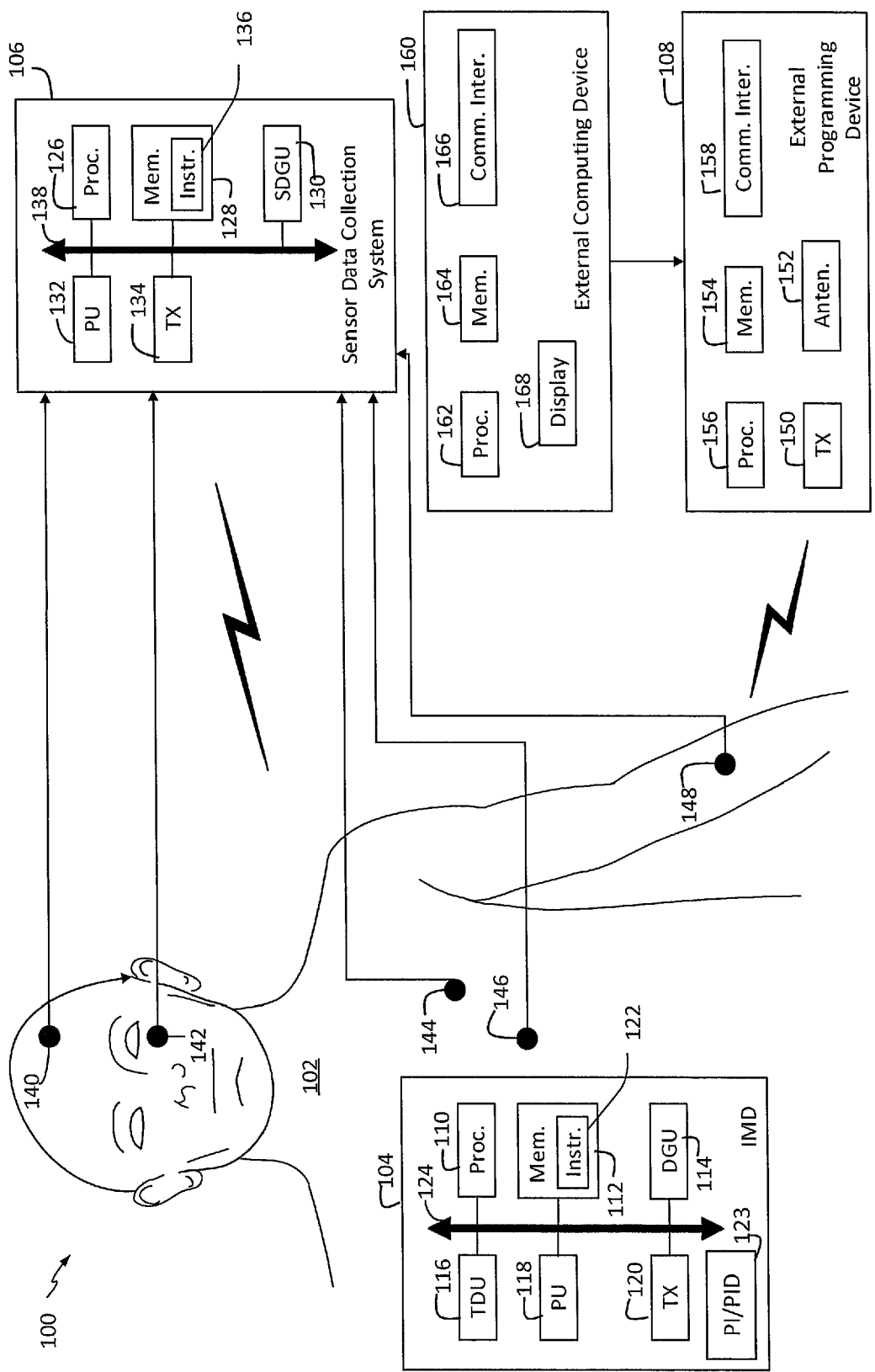
FIG. 1 is a block diagram of a particular embodiment of a system that uses cranial nerve stimulation to treat seizures.

Disclosed embodiments may enable providing improved therapeutic neurostimulation treatments for a variety of medical conditions based on synchronicity between neural activity of one or more regions of a patient's autonomic nervous system (e.g., the NTS) and one or more regions of the central nervous system (e.g., the thalamus and the cortex) of the patient.

As used herein, a "stimulation signal" refers to an electrical stimulation signal delivered to a portion of a patient's body to treat a medical condition by providing a modulating effect to neural tissue. A stimulation signal may be a Cranial Nerve Stimulation (CNS) signal, and the stimulation signal may be applied directly or indirectly to a cranial nerve. A stimulation signal may be a microburst signal, a non-microburst signal, or a combination. The effect of a stimulation signal on neuronal activity is termed "modulation;" however, for simplicity, the terms "stimulating" and "modulating," and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking; (c) affecting changes in neurotransmitter/neuromodulator release or uptake; and (d) changes in neuro-plasticity or neurogenesis of brain tissue.

As used herein, the autonomic nervous system (ANS or visceral nervous system or involuntary nervous system) is the part of the peripheral nervous system that acts as a control system that functions largely below the level of consciousness to control visceral functions, including heart rate, digestion, respiratory rate, salivation, perspiration, pupillary dilation, micturition (urination), sexual arousal, breathing and swallowing. Most autonomous functions are involuntary but they can often work in conjunction with the somatic nervous system which provides voluntary control.

Within the brain, the ANS is located in the medulla oblongata in the lower brainstem. The medulla's major ANS functions include respiration (the respiratory control center, or "rec"), cardiac regulation (the cardiac control center, or "ccc"), vasomotor activity (the vasomotor center or "vmc"), and certain reflex actions (such as coughing, sneezing, vomiting and swallowing). Those are then subdivided into other areas and are also linked to ANS subsystems and nervous systems external to the brain. The hypothalamus, just above the brain stem, acts as an integrator for autonomic functions, receiving ANS regulatory input from the limbic system to do so.

The ANS is divided into three main sub-systems: the parasympathetic nervous system (PSNS), the sympathetic nervous system (SNS), and the enteric nervous system (ENS). Depending on the circumstances, these sub-systems may operate independently of each other or interact co-operatively. Seizure origination and/or propagation may functionally impair neural circuits involved in the regulation of an autonomic function. Therefore, understanding the relationship between the autonomic nervous system and the central nervous system may help improve the understanding of the underlying pathology associated with seizures as well as the efficacy of the therapy applied in order to abort seizures and/or alleviate the overall seizure burden.

As used herein, the term "microburst" refers to at least a portion of a stimulation signal including a limited plurality of pulses and a limited duration. A micro burst may include at least two pulses per burst. In some embodiments, a microburst may include no more than about 25 electrical pulses per burst. In some embodiments, a microburst may have from 2 to about 20 pulses per burst. In some embodiments, a microburst may have from 2 to about 15 pulses per burst. A micro burst may last for no more than 1 second, typically less than 100 milliseconds, e.g., from about 10 msec to about 80 msec. A micro burst signal may include a series of microbursts separated from one another by time intervals known as "interburst periods." The interburst periods may allow a refractory interval for the nerve to recover from the microburst and again become receptive to electrically elicited visual evoked potential (e VEP) stimulation by another microburst. In some embodiments, an interburst period may be as long as or longer than adjacent micro bursts (e.g., micro bursts separated by the interburst period). In some embodiments an interburst period may have an absolute time period (e.g., duration) of at least 100 milliseconds. Adjacent pulses in a microburst are separated by a time interval known as an "interpulse interval." A "micro burst duration" is a length of a micro burst from the beginning of the first pulse of a micro burst to the end of the last pulse of the micro burst (and thus the beginning of a new interburst period). A microburst duration may be defined using the microburst's interpulse interval, together with the number of pulses and the pulse width of each pulse. Microburst signals may thus be characterized by an interburst period, a microburst duration, a number of pulses per microburst, and an interpulse interval. The pulses in a microburst may be further characterized by a current amplitude and a pulse width. Electrical stimulation according to disclosed embodiments may optionally include an on-time and an off-time in which the microbursts are provided and not provided, respectively, to a cranial nerve.

In some embodiments, microburst cranial nerve stimulation may be applied to a patient's cranial nerve by applying a microburst signal to the patient's cranial nerve. As explained above, the microburst signal may be a pulsed signal including a series of microbursts separated by interburst periods. In some embodiments, the interburst periods may have a duration of at least 100 milliseconds each. In other embodiments, the interburst periods may have a duration of at least the length of one of two microbursts separated by the interburst period. In another embodiment, the interburst period may be determined for a particular patient by providing microbursts separated by increasingly smaller interburst periods. The interburst period may be provided as any time interval greater than that at which the e VEP significantly diminishes or disappears. Each micro burst comprises a number of pulses per micro burst, an interpulse interval, and has a micro burst duration. In some embodiments, the number of pulses per micro burst may range from 2 to about 25 pulses, and in another embodiment the number of pulses per micro burst may range from 2 to about 20 pulses, preferably from 2 to about 15 pulses. The microbursts may be applied to a portion of a cranial nerve of the patient. At least one of the interburst period, the number of pulses per microburst, the interpulse interval, or the microburst duration may be selected to enhance cranial nerve evoked potentials.

Pulses within a microburst may also have a pulse width and a current amplitude. In some embodiments, the method may also comprise an off-time, during which microbursts are not applied to the patient and an on-time during which microbursts are applied to the patient. It may be convenient to refer to a burst frequency, defined as 1 divided by the sum of the micro burst duration and the interburst period, and it will be recognized by persons of skill in the art that the interburst period may alternatively be described in terms of a frequency of the pulses rather than as an absolute time separating one pulse from another. Pulse shapes in electrical signals may include a variety of shapes including square waves, biphasic pulses (including active and passive charge-balanced biphasic pulses), triphasic waveforms, etc. In one embodiment, the pulses comprise a square, biphasic waveform in which the second phase is a charge-balancing phase of the opposite polarity to the first phase.

In some embodiments, conventional cranial nerve stimulation (e.g., "non-microburst" stimulation) may be applied. In this case, a non-microburst signal may be defined by a current amplitude, a pulse width, a frequency, an on-time, and an off-time. The non-microburst signal typically has more than about 50 pulses per burst and a burst duration of at least about 7 seconds.

In some embodiments, a method may include applying a primary mode of cranial nerve stimulation during a first period and a secondary mode of cranial nerve stimulation during a second period. In some embodiments, the primary mode may be conventional cranial nerve stimulation (e.g., stimulation by application of one or more non-micro burst signals), and the secondary mode may be microburst cranial nerve stimulation (e.g., stimulation by application of one or more microburst signals). In other embodiments, the primary mode may be microburst cranial nerve stimulation and the secondary mode may be conventional cranial nerve stimulation. When the primary mode is conventional cranial nerve stimulation, the first period may correspond to the on-time of conventional cranial nerve stimulation and the second time period may correspond to the off-time of conventional cranial nerve stimulation. In another embodiment, the first period and the second period can partially overlap. In another embodiment, one of the first period or the second period can be entirely overlapped by the other of the first period or the second period.

Referring to FIG. 1, a block diagram of a system 100 that uses CNS to treat seizures of a patient 102 (e.g., an epilepsy patient) is shown according to an exemplary embodiment. CNS may include vagus nerve stimulation (VNS), trigeminal nerve stimulation (TNS), stimulation of other cranial nerves, or a combination thereof. The system 100 may include an implantable medical device (IMD) 104, a sensor data collection system 106, and an external programming device 108. The IMD 104 may include a processor 110, a memory 112, a data gathering unit 114, a therapy delivery unit (TDU) 116, a power storage unit 118, a transceiver 120, and a system bus 124. The processor 110 may be a single processor of the IMD 104 or multiple processors of the IMD 104. The memory 112 may include instructions 122 that are executable by the processor 110 to operate the IMD 104. The system 100 may include a controller 123 of a feedback control loop, which may be a part of (or operate in conjunction with) the processor 110 and the memory 112. In some embodiments, the controller 123 may include software (instructions) stored in the memory 112 and executable by the processor 110.

The data gathering unit 114 may gather data related to an operational state of the IMD 104 (e.g., a charge state of the power storage unit 118), data related to therapy provided to the patient 102, body parameter data corresponding to one or more body parameters of the patient 102, or a combination thereof. Data gathered by the data gathering unit 114 may be used to control therapy provided to the patient 102, may be transmitted to an external device, or both.

The TDU 116 may be configured to provide therapy to the patient 102. For example, the TDU 116 may provide electrical stimulation (via one or more electrodes (not shown)) to tissue of the patient 102. The TDU 116 may provide electrical stimulation to the cranial nerve (e.g., the vagus nerve, the trigeminal nerve, etc.) of the patient 102. Therapy provided by the TDU 116 may be controlled by the processor 110. The power storage unit 118 may provide electrical power to components of the IMD 104 and/or to the IMD 104. For example, the power storage unit 118 may be a battery. The transceiver 120 may enable the IMD 104 to communicate with other devices, such as the sensor data collection system 106 and the external programming device 108. The processor 110, the memory 112, the data gathering unit 114, the TDU 116, the power storage unit 118, and the transceiver 120 may be connected via the system bus 124.

The sensor data collection system 106 may include a processor 126, a memory 128, a sensor data gathering unit 130, a power storage unit 132, a transceiver 134, and a system bus 138. The processor 126 may be a single processor of the sensor data collection system 106 or may include multiple processors of the sensor data collection system 106.

The memory 128 may include instructions 136 that are executable by the processor 126 to operate the sensor data collection system 106.

The sensor data gathering unit 130 may be configured to collect body parameter data from one or more sensors placed on, in, and/or near the patient 102. Activity of one or more regions of the patient's central nervous system and/or one or more regions of the patient's autonomic nervous system may be measured using body parameter data collected from sensors placed in the patient's central nervous system and/or autonomic nervous system. Alternatively, or in addition, activity in the patient's central nervous system and/or autonomic nervous system may be measured using body parameter data collected form sensors that are placed on the surface of the body of the patient. For example, surface electrodes placed on the head of the patient may be used to record a far-field visual evoked potential (VEP), which originates from regions of the forebrain, using EEG equipment typically used clinically for recording somatosensory or auditory evoked potentials.

As examples, an electroencephalography (EEG) sensor(s) 140, an electrooculography (EOG) sensor(s) 142, an electrocardiography (ECG) sensor(s) 144, an electromyography (EMG) sensor(s) 146, and an accelerometer(s) 148 may be placed on the patient 102 to sense a body parameter data of the patient 102, or a part of the patient 102. A first sensor may be placed in, on or near the patient 102 to sense a body parameter data of at least a portion of the patient's central nervous system. A second sensor may be placed in, on or near the patient 102 to sense body parameter data of at least a portion of the patient's autonomic nervous system. The body parameter data may include EEG data, EOG data, ECG data, respiration data, EMG data, accelerometer data, or a combination thereof. In some embodiments, the body parameter data may include EEG data indicative of neural activity of (or associated with) the patient's central nervous system and local field potentials or spiking activity data indicative of neural activity of (or associated with) the patient's autonomic nervous system. The sensor data gathering unit 130 may receive the body parameter data via respective wired or wireless connections to the EEG sensor(s) 140, the EOG sensor(s) 142, the ECG sensor(s) 144, the EMG sensor(s) 146, and the accelerometer(s) 148.

In some embodiments, body parameter data may include spike train data indicative of a sequence of neuronal action potentials of one or more neurons in one or more regions of the patient's autonomic nervous system and spike train data indicative of a sequence of neuronal action potentials of one or more neurons in one or more regions of the patient's central nervous system.

In some embodiments, body parameter data may include a neuronal firing rate of one or more neurons of one or more regions of the patient's central nervous system and a neuronal firing rate one or more neurons of one or more regions of the patient's autonomic nervous system. In some embodiments, the body parameter data may include a continuous time series of brain activity associated with the patient's central nervous system and a continuous time series of brain activity associated with the patient's autonomic nervous system.

The power storage unit 132 may be configured to provide electrical power to components of the sensor data collection system 106 and/or to the sensor data collection system 106. For example, the power storage unit 132 may include a battery. The transceiver 134 may be configured to enable the sensor data collection system 106 to communicate with other devices, such as the IMD 104 and the external programming device 108. The processor 126, the memory 128, the sensor data gathering unit 130, the power storage unit 132, and the transceiver 134 may be connected via the system bus 138.

The external programming device 108 may include a transceiver 150 and an antenna 152. The transceiver 150 may be configured to communicate (e.g., transmit data, receive data, or a combination thereof) via the antenna 152 with the IMD 104. For example, the external programming device 108 may send program data, such as therapy parameter data to the IMD 104 using wireless signals. The program data may be stored at a memory 158 of the external programming device 108, may be received from a computing device 160, or both.

The external computing device 160 may include a processor 162, a memory 164, a communication interface 166, a display 168, other components (not shown), or a combination thereof. The external computing device 160 may receive data from the external programming device 108, the sensor data collection system 106, the IMD 104, or a combination thereof, via the communication interface 166 and may store the data in the memory 164. The external computing device 160 may provide an interface (e.g., via the display 168) to the patient 102 and/or to a health care provider to see the stored data. The stored data may be used to facilitate determining information regarding efficacy of a therapy.

During operation, the sensor data collection system 106 may collect the body parameter data from the EEG sensor(s) 140, the EOG sensor(s) 142, the ECG sensor(s) 144, the EMG sensor(s) 146, the accelerometer 148, or a combination thereof. In a particular embodiment, the sensor data collection system 106 may collect body parameter data from one or more areas of the patient's body other than the patient's brain. The sensor data collection system 106 may measure body parameter data in the form of neural activity at the patient's autonomic nervous system and neural activity at the patient's central nervous system. The sensor data collection system 106 may communicate the body parameter data to the IMD 104 occasionally (e.g., periodically) or continuously. The sensor data collection system 106 may communicate the body parameter data to the IMD 104 in real time (e.g., as soon as the sensor data collection system 106 receives the body parameter data) or in near-real time (e.g., after performing pre-processing such as filtering, grouping (such as by window), formatting, or a combination thereof).

A measurement indicative of synchrony between neural activity of one or more regions of the autonomic nervous system of the patient 102 and one or more regions of the central nervous system of the patient may sometimes be referred to herein as a "synchrony measurement." Based on the body parameter data, the IMD 104 (e.g., the processor 110) determines a measurement (e.g., a "first synchrony measurement") indicative of synchrony between neural activity of one or more regions of the autonomic nervous system of the patient 102 and one or more regions of the central nervous system of the patient 102 for a window (e.g., a "first window") of body parameter data. The first window may correspond to a particular time span during which body parameter data is gathered. Alternatively, the first window may be defined based on a parameter other than time, such as one or more stimulation parameters. For example, a first window may begin at a start of an on-time period of a stimulation signal and may end at a start of an off-time period of the stimulation signal. The first synchrony measurement may be in the form of a rate of change of a value indicative of synchrony between neural activity of one or more regions of the patient's autonomic nervous system and one or more regions of the patient's central nervous system during the first window. The first synchrony measurement may also, or in the alternative, be in the form of a measure of latency of communication between one or more regions of the patient's autonomic nervous system and one or more regions of the patient's central nervous system during the first window. The first synchrony measurement may also, or in the alternative, be determined using body parameter data collected by the sensor data collection system 106 from one or more areas of the patient's body other than the patient's brain (e.g., heart rate variability data, heart rate morphology data, or a combination thereof). The first synchrony measurement may also, or in the alternative, be determined using measurements collected by the sensor data collection system 106 of neural activity at the patient's autonomic nervous system and the patient's central nervous system.

The IMD 104 may determine the first synchrony measurement using a linear measure (e.g., cross-correlation and coherence) or nonlinear measure (e.g., mutual information, transfer entropy, granger causality, nonlinear interdependence, and phase synchronization) of the body parameter data. For example, the IMD 104 may determine the first synchrony measurement by determining a cross-correlation of data indicative of neuronal firing rates of one or more neurons of one or more regions of the patient's central nervous system during the first window and data indicative of neuronal firing rates of one or more neurons of one or more regions of the patient's autonomic nervous system during the first window.

The IMD 104 may determine the first synchrony measurement using time-scale dependent spike train distances (e.g., Victor-Purpura distance, van Rossum distance, Schreiber et al. similarity measure, Population extensions) or using time-scale independent spike train distances (e.g., Event synchronization, !SI-distance, SPIKE-distance). For example, the IMD 104 may determine the first synchrony measurement by determining a Victor-Purpura distance of spike train data for one or more regions of a patient's autonomic nervous system during the first window and spike train data for one or more regions of a patient's central nervous system during the first window.

Based on the first synchrony measurement, the IMD 104 may apply one or more stimulation signals (e.g., a "first stimulation signal") to a cranial nerve (e.g., vagus nerve) of the patient 102. When applied to the patient, the one or more stimulation signals may change the synchrony between neural activity of one or more regions of the patient's autonomic nervous system and one or more regions of the patient's central nervous system. For example, the one or more stimulation signals may include one or more microburst signals, and applying the one or more micro burst signals may increase synchrony between neural activity of one or more regions of the patient's autonomic nervous system and one or more regions of the patient's central nervous system.

The IMD 104 (e.g., the TDU 116) may apply the one or more stimulation signals to the patient based on a determination by the processor 110 that the first synchrony measurement indicates a seizure state (e.g., ongoing seizure, onset of a seizure, and/or imminent onset of a seizure) or non-seizure state (e.g., no ongoing seizure, seizure termination, and/or imminent termination of a seizure). In some embodiments, the threshold value may be a value indicative of a threshold level of synchrony (e.g., a "threshold synchrony value") between neural activity of one or more regions of the patient's autonomic nervous system and one or more regions of the patient's central nervous system.

In some embodiments, the processor 110 may determine that the first synchrony measurement indicates a seizure state by determining that the first synchrony measurement satisfies a threshold synchrony value indicative of onset of a seizure. For example, onset of a seizure may be indicated by a low (relative to a non-seizure state) synchrony between neural activity of one or more regions of the patient's autonomic nervous system and one or more regions of the patient's central nervous system. Thus, the threshold synchrony level may be selected to correspond to a low (relative to a non-seizure state) level of synchrony between one or more regions of the patient's autonomic nervous system and one or more regions of the patient's central nervous system. The first synchrony measurement may be determined to satisfy the threshold synchrony value when the first synchrony measurement (e.g., using the processor 110) indicates that synchrony between neural activity of one or more regions of the patient's autonomic nervous system and one or more regions of the patient's central nervous system is below the threshold synchrony value. For example, the IMD 104 may apply one or more microburst signals to a patient's vagus nerve in response to the processor 110 determining that the first synchrony measurement indicates that synchrony between neural activity of one or more regions of the patient's autonomic nervous system and one or more regions of the patient's central nervous system satisfies (e.g., is below) a threshold synchrony value indicative of onset of a seizure.

As a further example, onset of a seizure may be indicated by synchrony between neural activity of one or more regions of the patient's autonomic nervous system and one or more regions of the patient's central nervous system that decreases at a rate greater than or equal to a rate corresponding to a threshold synchrony value (in the form of a rate of change as described above). Thus, a threshold synchrony value indicative of a seizure state (e.g., seizure onset) may be selected to correspond to a rate of change (e.g., rate of decrease) of synchrony between neural activity of one or more regions of the patient's autonomic nervous system and one or more regions of the patient's central nervous system. The first synchrony measurement (e.g., in the form of a rate of change of synchrony) may be determined to satisfy the threshold synchrony level when the first synchrony measurement (e.g., using the processor 110) indicates that the synchrony between the neural activity of one or more regions of the patient's autonomic nervous system and one or more regions of the patient's central nervous system is decreasing at a rate at least as fast the threshold synchrony value. For example, the IMD 104 may apply one or more microburst signals to a patient's vagus nerve in response to the processor 110 determining that the first synchrony measurement indicates that synchrony between neural activity of one or more regions of the patient's autonomic nervous system and one or more regions of the patient's central nervous system satisfies (e.g., is decreasing at a rate equal to or greater than) the threshold synchrony value.

In some embodiments, the processor 110 may determine that the first synchrony measurement indicates a non-seizure state by determining that the first synchrony measurement satisfies a threshold synchrony value indicative of termination of a seizure. For example, termination of a seizure may be indicated by higher (relative to when the patient is experiencing a seizure) synchrony between neural activity of one or more regions of the patient's autonomic nervous system and one or more regions of the patient's central nervous system. Thus, the threshold synchrony level may be selected to correspond to a higher (relative to a seizure state) level of synchrony between one or more regions of the patient's autonomic nervous system and one or more regions of the patient's central nervous system. The first synchrony measurement may be determined to satisfy the threshold synchrony value when an evaluation of the first synchrony measurement (e.g., using the processor 110) indicates that the synchrony between neural activity of one or more regions of the patient's autonomic nervous system and one or more regions of the patient's central nervous system is above the threshold synchrony value. For example, the IMD 104 may apply one or more microburst stimulation signals to a patient's vagus nerve until the processor 110 determines that a synchrony measurement of the patient indicates that synchrony between neural activity of one or more regions of the patient's autonomic nervous system and one or more regions of the patient's central nervous system satisfies (e.g., exceeds) a threshold synchrony value indicative of a non-seizure state (e.g., that the patient's seizure has ended).

As a further example, termination of a seizure may be indicated by synchrony between neural activity of one or more regions of the patient's autonomic nervous system and one or more regions of the patient's central nervous system that increases at least at a rate corresponding to a threshold synchrony value. Thus, a threshold synchrony value indicative of a non-seizure state (e.g., seizure termination) may be selected to correspond to a rate of change (e.g., rate of increase) of synchrony between neural activity of one or more regions of the patient's autonomic nervous system and one or more regions of the patient's central nervous system. The first synchrony measurement (e.g., in the form of a rate of change of synchrony) may be determined to satisfy the threshold synchrony value when an evaluation of the first synchrony measurement (e.g., using the processor 110) indicates that the synchrony between the neural activity of one or more regions of the patient's autonomic nervous system and one or more regions of the patient's central nervous system is increasing at a rate at least as fast the threshold synchrony value. For example, the IMD 104 may apply one or more microburst signals to a patient's vagus nerve in response to the processor 110 determining that the first synchrony measurement indicates that synchrony between neural activity of one or more regions of the patient's autonomic nervous system and one or more regions of the patient's central nervous system satisfies (e.g., is increasing at a rate greater than) the threshold synchrony value.

Alternatively, or in addition, based on the first synchrony measurement, the IMD 104 may change its stimulation mode from a first stimulation mode (e.g., a micro burst stimulation mode) to a second stimulation mode (e.g., a non-microburst stimulation mode). In a microburst stimulation mode, the IMD 104 (e.g., TDU 116) is configured to apply one or more microburst signals to a cranial nerve of the patient, and in a non-micro burst stimulation mode, the IMD 104 (e.g., TDU 116) is configured to apply one or more non-microburst signals to a cranial nerve of the patient.

The IMD 104 may change its stimulation mode from the first stimulation mode to the second stimulation mode based on a determination by the processor 110 that the first synchrony measurement satisfies a threshold value. In some embodiments, the threshold value may be a threshold synchrony value.

In some embodiments, the threshold synchrony value may be a value indicative of a seizure state (e.g., onset or imminent onset of a seizure). For example, the IMD 104 may be operating, or set to operate, in a non-microburst stimulation mode prior to determining that the first synchrony measurement satisfies a threshold synchrony value indicative of onset of a seizure. Based on determining that the first synchrony measurement satisfies the threshold synchrony value, the IMD 104 may change its stimulation mode from the non-micro burst stimulation mode to the micro burst stimulation mode (e.g., the IMD 104 may instruct the TDU 116 to apply one or more microburst signals to a patient's vagus nerve in response to the processor 110 determining that the first synchrony measurement satisfies the threshold synchrony value). Alternatively, the IMD 104 may be operating, or set to operate, in a microburst stimulation mode prior to determining that the first synchrony measurement satisfies the threshold synchrony value indicative of onset of a seizure. Based on determining that the first synchrony measurement satisfies the threshold synchrony value, the IMD 104 may change its stimulation mode from the microburst stimulation mode to the non-microburst stimulation mode (e.g., the IMD 104 may instruct the TDU 116 to apply one or more non-micro burst signals to a patient's vagus nerve in response to the processor 110 determining that the first synchrony measurement satisfies the threshold synchrony value).

In some embodiments, the threshold synchrony value may be a value indicative of a non-seizure state (e.g., termination of a seizure). For example, the IMD 104 may be operating, or set to operate, in a non-microburst stimulation mode prior to determining that the first synchrony measurement satisfies a threshold synchrony value indicative of termination of a seizure. Based on determining that the first synchrony measurement satisfies the threshold synchrony value, the IMD 104 may change its stimulation mode from the non-microburst stimulation mode to the micro burst stimulation mode (e.g., the IMD 104 may instruct the TDU 116 to apply one or more microburst signals to a patient's vagus nerve in response to the processor 110 determining that the first synchrony measurement satisfies the threshold synchrony value). Alternatively, the IMD 104 may be operating, or set to operate, in a micro burst stimulation mode prior to determining that the first synchrony measurement satisfies the threshold synchrony value indicative of termination of a seizure. Based on determining that the first synchrony measurement satisfies the threshold synchrony value, the IMD 104 may change its stimulation mode from the micro burst stimulation mode to the non-micro burst stimulation mode (e.g., the IMD 104 may instruct the TDU 116 to apply one or more non-microburst signals to a patient's vagus nerve in response to the processor 110 determining that the first synchrony measurement satisfies the threshold synchrony value).

The IMD 104 may additionally determine a synchrony measurement (e.g., a "second synchrony measurement") after application of a first stimulation signal of the one or more stimulation signals is initiated. The second synchrony measurement may be based on body parameter data collected by the sensor data collection system 106 after application of the first stimulation signal is initiated (e.g., for a "second window" of body parameter data that begins after application of the first signal is initiated). The second window may correspond to a particular time span during which body parameter data is gathered. Alternatively, the second window may be defined based on a parameter other than time, such as one or more stimulation parameters. For example, the second window of body parameter data may begin at a start of an on-time period of the stimulation signal and may end at a start of an off-time period of the first stimulation signal. The second synchrony measurement may be provided to the controller 123 of the feedback control loop that determines a stimulation parameter of a second stimulation signal, determines whether to change a stimulation mode, or both. The controller 123 may be a proportional/integral (PI) controller, a proportional/integral/derivative (PID) controller, or some other controller that functions as described in greater detail with reference to FIG. 2.

Figure 2:
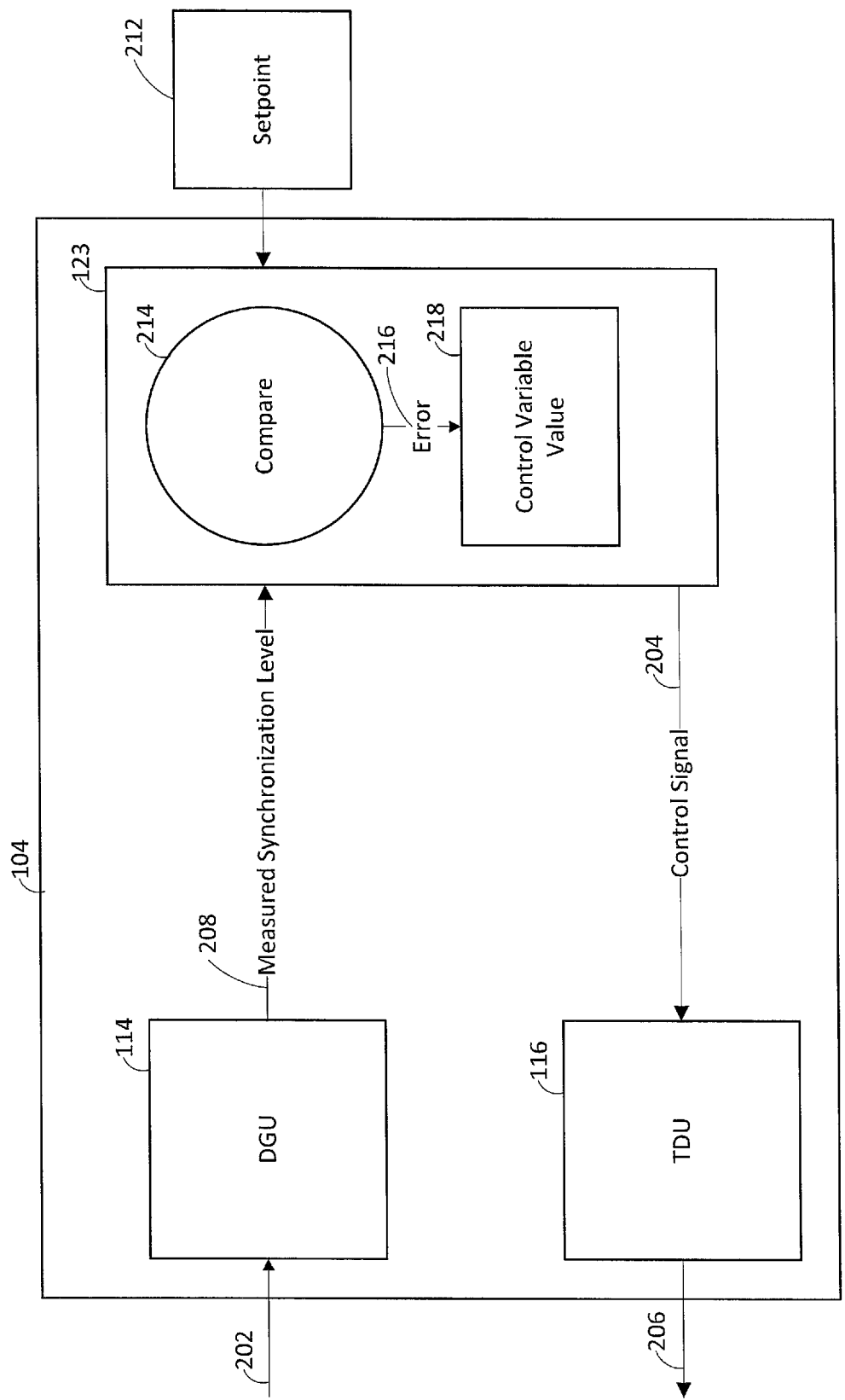
FIG. 2 is a block diagram of a particular embodiment of a device that uses cranial nerve stimulation to treat seizures.

FIG. 2 is a block diagram of a particular embodiment of an IMD 104 of FIG. 1 that includes a controller 123 to determine one or more parameters of the second stimulation signal, whether to change a simulation mode of the IMD, or both. The controller 123 may be a part of (or operate in conjunction with) the processor 110 and the memory 112 of FIG. 1. In some embodiments, the controller 123 may include software (instructions) stored in the memory 112 and executable by the processor 110 of FIG. 1. With reference to FIG. 2, the data gathering unit 114 may receive body parameter data or other measurements 202 from the sensor data collection system 106 of FIG. 1, and may output a "second synchrony measurement" 208 to the controller 123. In some embodiments, the data gathering unit 114 processes the body parameter data 114 in conjunction with the processor 110 to determine the second synchrony measurement from the received body parameter data 114. The controller 123 compares, at 214, the second synchrony measurement 208 to a setpoint 212 to determine an error value 216. The setpoint 212 may be a value indicative of a baseline synchrony level of the patient, e.g., a value indicative of a synchrony level of the patient prior to seizure onset. The setpoint 212 may be a predicted value. For example, the setpoint 212 may correspond to a synchrony level that is predicted by a model to present in response to application of the first stimulation signal to the patient. The error value 216 may be processed by the controller 123 to determine a control variable value 218. The controller 123 may use the control variable value 218 to determine a value of at least one stimulation parameter of a second stimulation signal. Alternatively, or in addition, the controller 123 may use the control variable value to determine a stimulation mode of the IMD 104 (e.g., microburst stimulation mode or non-microburst stimulation mode of the IMD 104). The controller 123 may provide a control signal 204 to the TDU 116. The TDU 116 may change its stimulation mode in response to receiving the control signal 204 indicative of the stimulation mode. The TDU 116 may apply a second stimulation signal to the patient. The second stimulation signal may have a value of a stimulation parameter based on stimulation parameter information from the control signal 204. For example, controller 123 may determine that, based on the input error value 216 and the parameters of the first stimulation signal, an amplitude of the second stimulation signal should be changed (e.g., increased) to a second value. The TDU 116 may apply the second stimulation signal 206 having an amplitude corresponding to the second value responsive to receiving the control signal 204.

FIGS. 3-8 illustrate exemplary body parameter data (e.g., spike train data) as spike train traces of one or more neurons during application of one or more non-microburst signals. The body parameter data in FIGS. 3-8 may be collected by the sensor data collection system 106 of FIG. 1 and provided to the IMD 104 of FIGS. 1 and 2.

Figure 3:
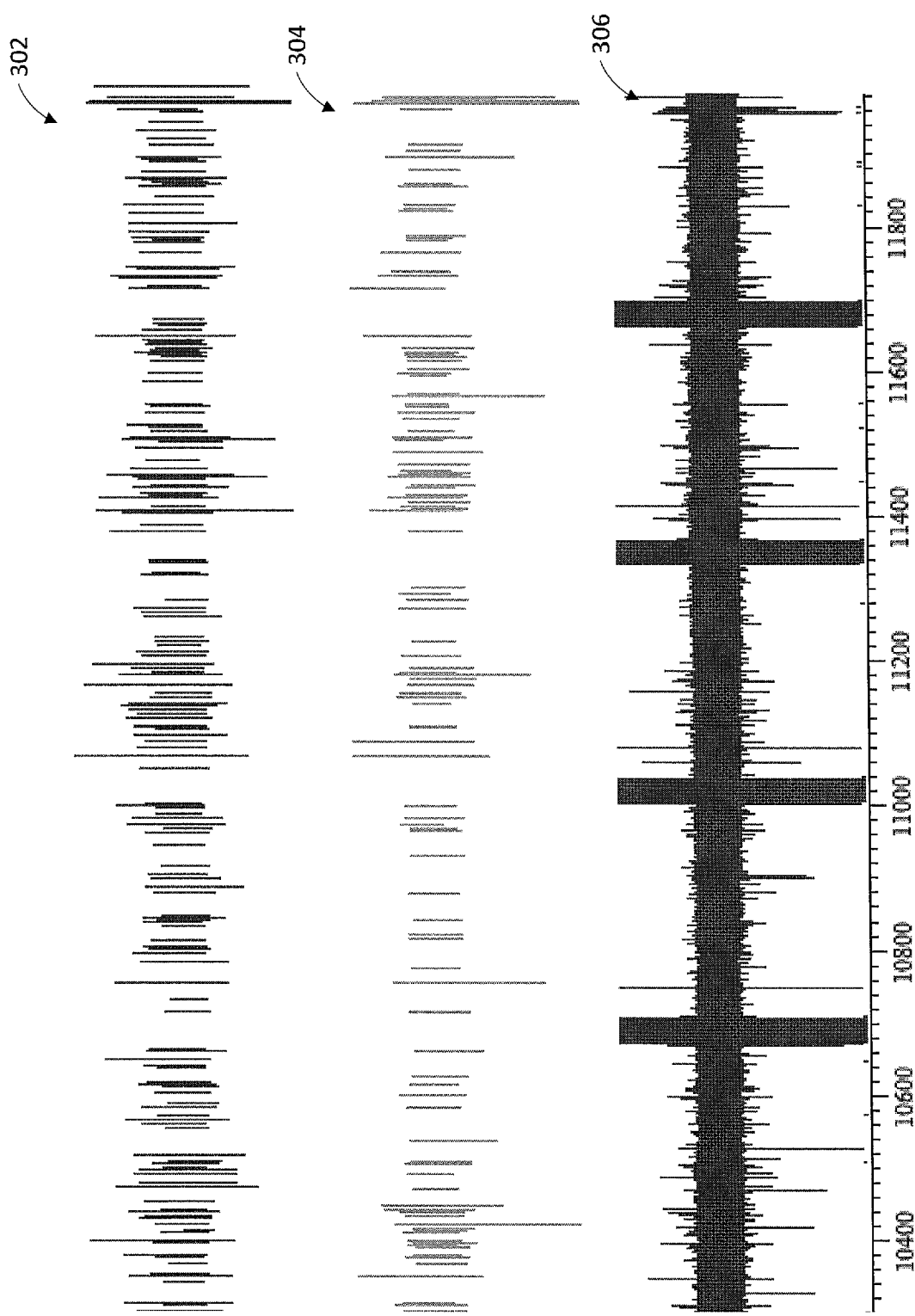
FIG. 3 is a diagram illustrating two cortical spike train traces during application of an exemplary non-microburst signal having an amplitude of 0.75 mA, a frequency of 30 Hz, a pulse width of 500 microseconds, an on time of 30 seconds, and an off time of 5 minutes.
Figure 4:
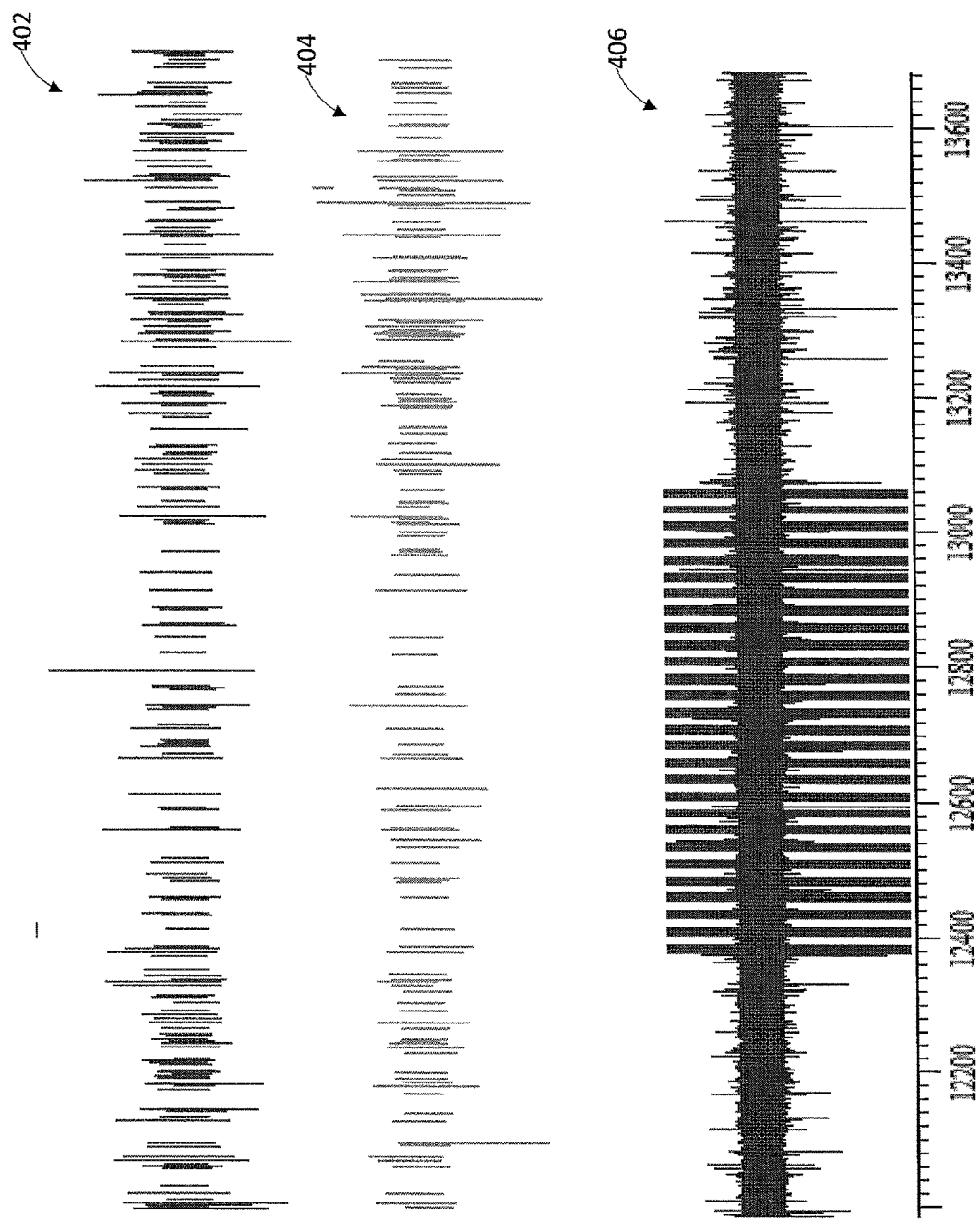
FIG. 4 is a diagram illustrating two cortical spike train traces during application of an exemplary non-microburst signal having an amplitude of 0.75 mA, a frequency of 30 Hz, a pulse width of 500 microseconds, an on time of 7 seconds, and an off time of 0.3 minutes.
Figure 5:
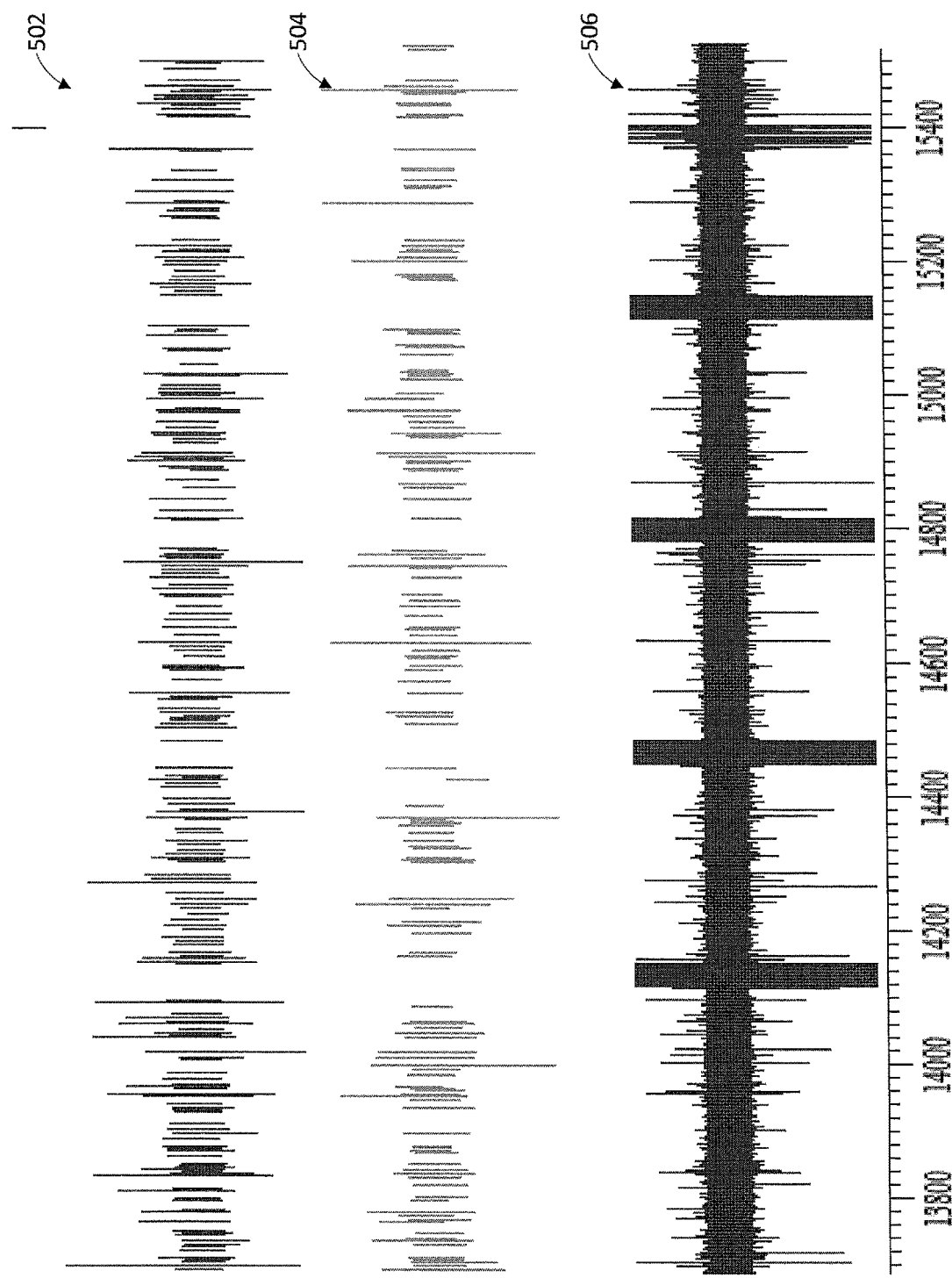
FIG. 5 is a diagram illustrating two cortical spike train traces during application of an exemplary non-micro burst signal having an amplitude of 1.25 mA, a frequency of 30 Hz, a pulse width of 500 microseconds, an on time of 30 seconds, and an off time of 5 minutes.

Spike train traces 302 and 304 of FIGS. 3, 402 and 404 of FIG. 4, and 502 and 504 of FIG. 5 illustrate spike train data as spike train traces of one or more neurons of a patient's parietal cortex during application of non-microburst signals 306, 406, and 506 to a vagus nerve, respectively. To gather the spike traces 302 and 304, the non-microburst signal 306 had the following stimulation parameters: 0.75 mA, 30 Hz, 500 microsecond pulsewidth, 30 second on-time, and 5 min off-time. To gather the spike traces 402 and 404, the non-microburst signal 406 had the following parameters: 0.75 mA, 30 Hz, 500 microsecond pulsewidth, 7 second on-time and 0.3 minute off-time. To gather the spike traces 502 and 504, the non-microburst signal 506 had the following parameters: 1.25 mA, 30 Hz, 500 microsecond pulsewidth, 30 second on-time and 5 minute off-time. As indicated by the spike traces of FIGS. 3-5, application of non-microburst signals does not elicit substantial cortical activation.

Figure 6:
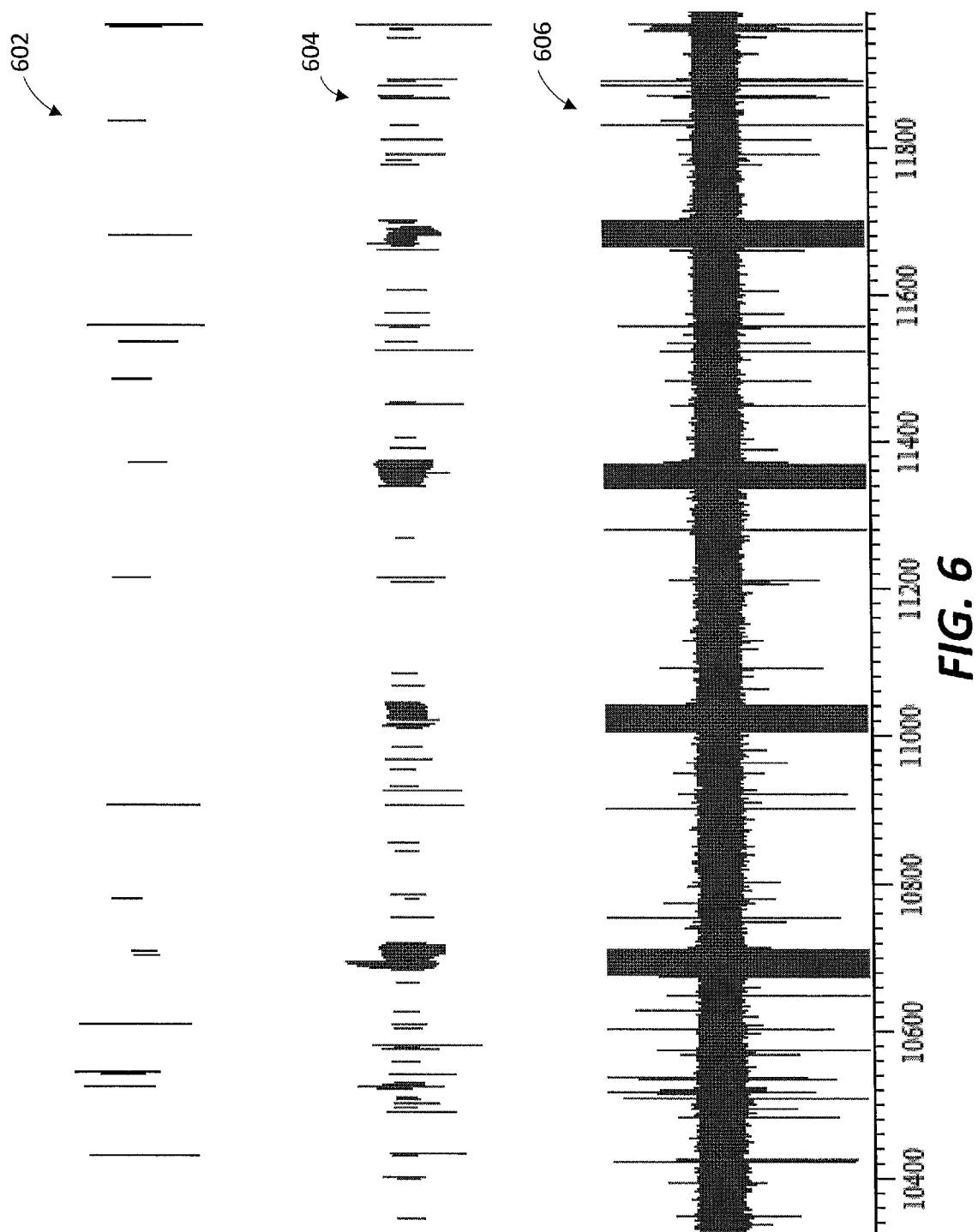
FIG. 6 is a diagram illustrating two NTS spike train traces during application of an exemplary non-microburst signal having an amplitude of 0.75 mA, a frequency of 30 Hz, a pulse width of 500 microseconds, an on time of 30 seconds, and an off time of 5 minutes.
Figure 7:
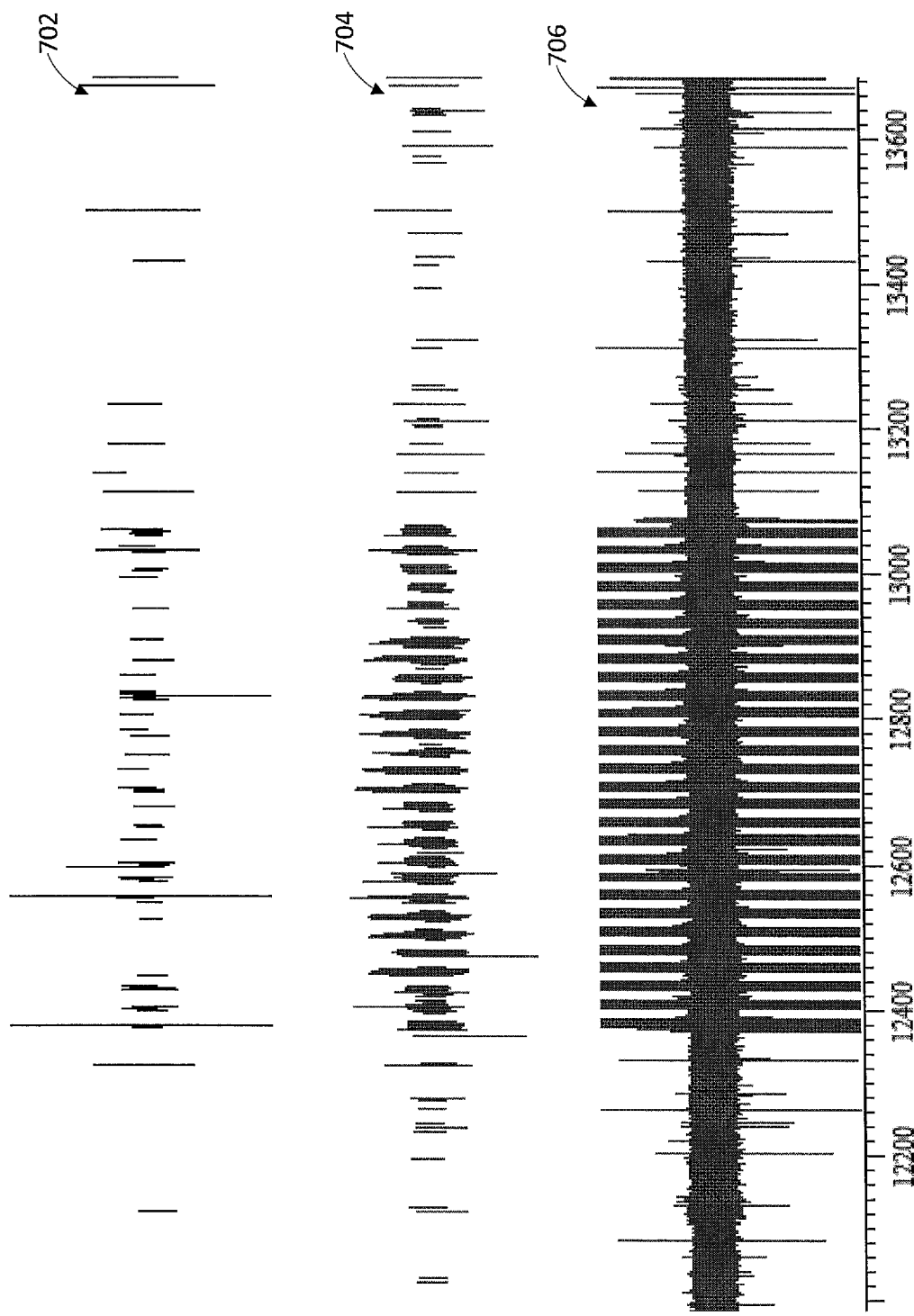
FIG. 7 is a diagram illustrating two NTS spike train traces during application of an exemplary non-microburst signal having an amplitude of 0.75 mA, a frequency of 30 Hz, a pulse width of 500 microseconds, an on time of 7 seconds, and an off time of 0.3 minutes.
Figure 8:
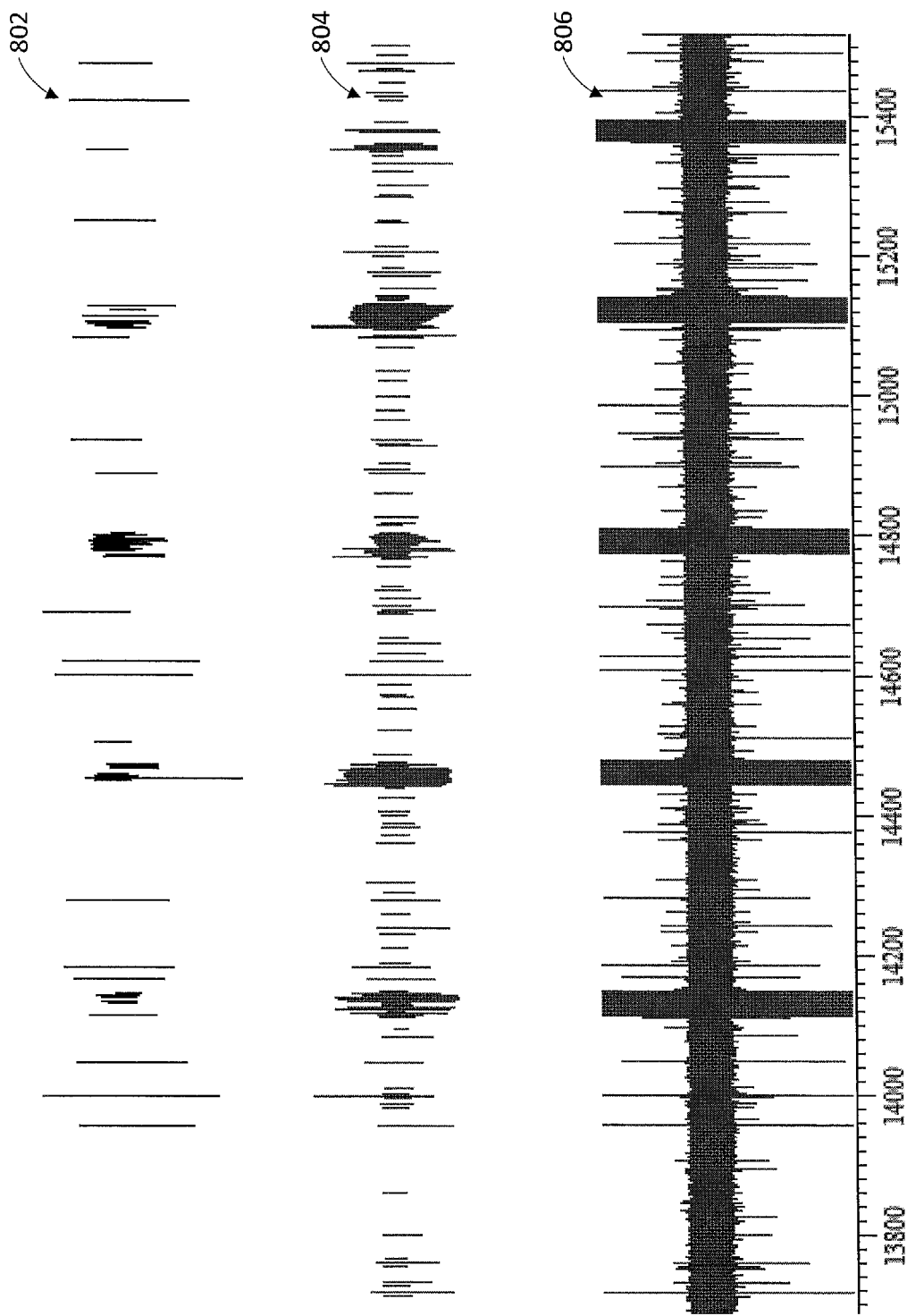
FIG. 8 is a diagram illustrating two NTS spike train traces during application of an exemplary non-micro burst signal having an amplitude of 1.25 mA, a frequency of 30 Hz, a pulse width of 500 microseconds, an on time of 30 seconds, and an off time of 5 minutes.
Figure 9:
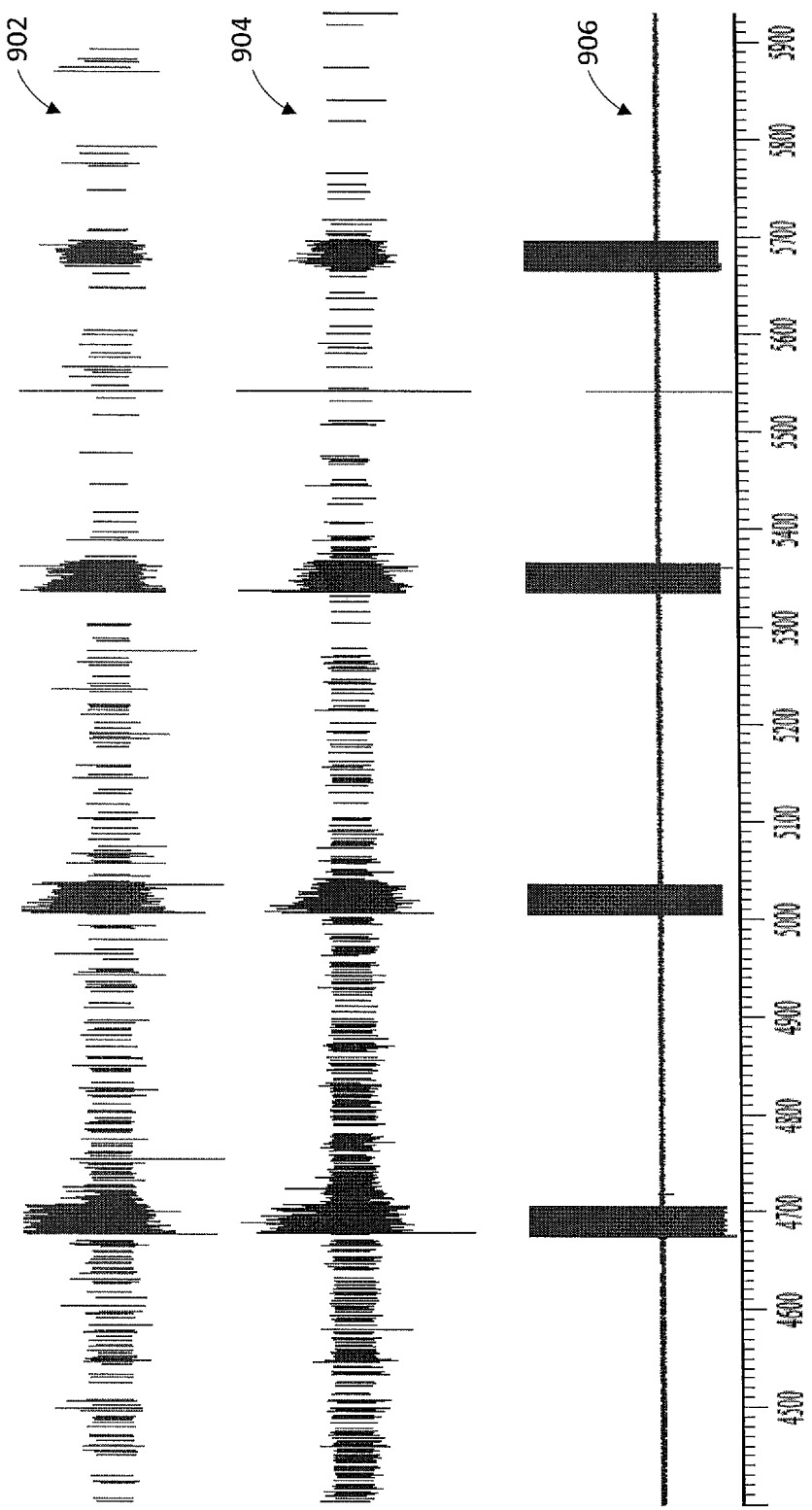
FIG. 9 is a diagram illustrating two cortical spike train traces during application of an exemplary microburst signal having 5 pulses per microburst, an amplitude of 0.75 mA, a frequency of 250 Hz, a pulse width of 500 microseconds, an interburst period of 0.5 seconds, an on time of 30 seconds, and an off time of 5 minutes.
Figure 10:
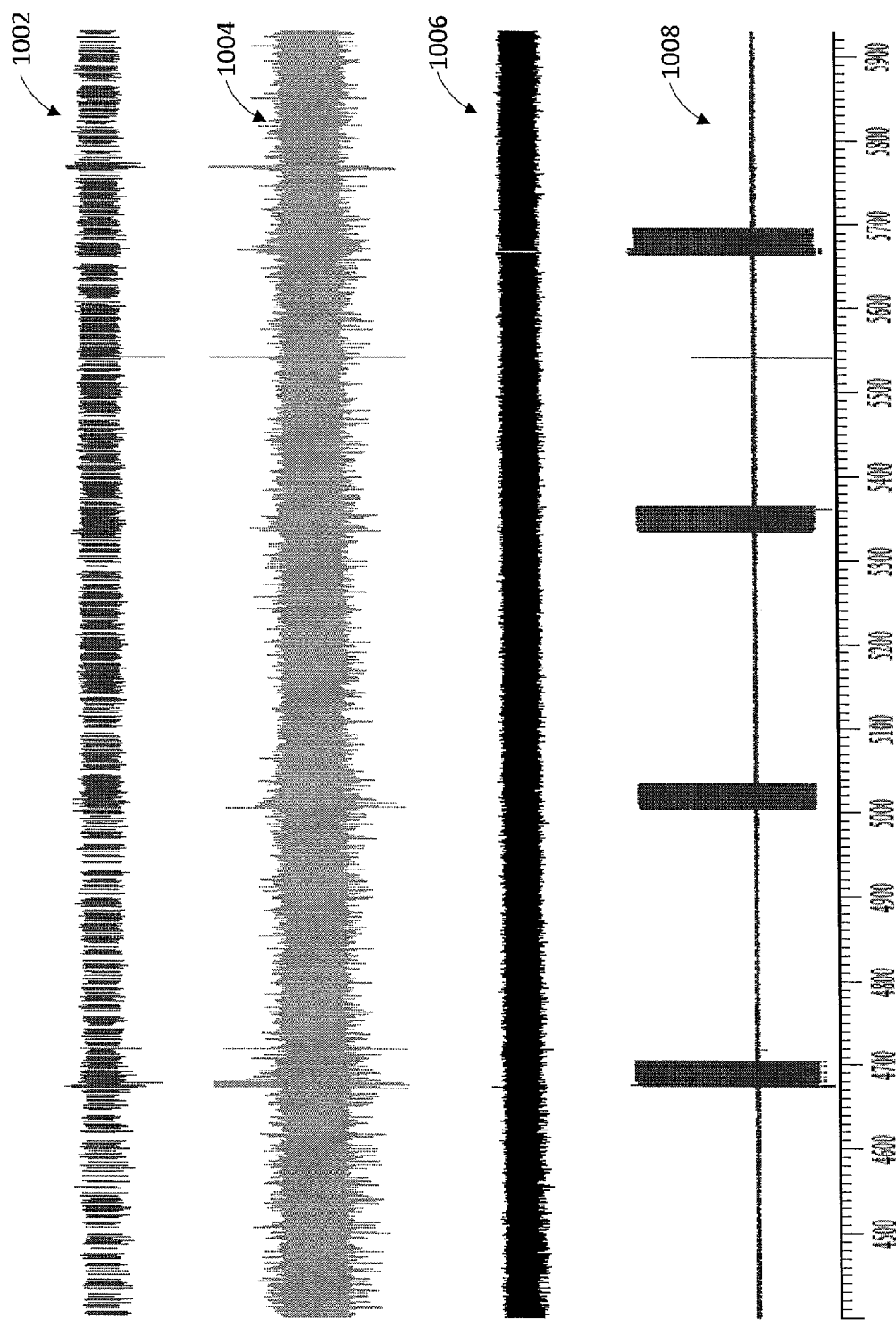
FIG. 10 is a diagram illustrating three NTS spike train traces during application of an exemplary microburst signal having 5 pulses per microburst, an amplitude of 0.75 mA, a frequency of 250 Hz, a pulse width of 500 microseconds, an interburst period of 0.5 seconds, an on time of 30 seconds, and an off time of 5 minutes.

Spike train traces 602 and 604 of FIGS. 6, 702 and 704 of FIG. 7, and 802 and 804 of FIG. 8 illustrate spike train data of one or more neurons of one or more regions of a patient's NTS during application of non-microburst signals 606, 706, and 806, respectively. To gather the spike traces 602 and 604, the non-microburst signal 606 had the following parameters: 0.75 mA, 30 Hz, 500 microseconds pulsewidth, 30 second on-time, and 5 minute off-time. To gather the spike traces 702 and 704, the non-microburst signal 706 had the following parameters: 0.75 mA, 30 Hz, 500 microseconds pulsewidth, 7 second on-time, and 0.3 minute off-time. To gather the spike traces 802 and 804, the non-microburst signal 806 had the following parameters: 1.25 mA, 30 Hz, 500 microseconds pulsewidth, 30 second on-time, and 5 min off-time. In contrast to response of the parietal cortex to application of non-microburst signals, application of non-microburst signals increased NTS neuronal activity significantly during the stimulation phase (as indicated by the spike traces of FIGS. 6-8).

Figure 11:
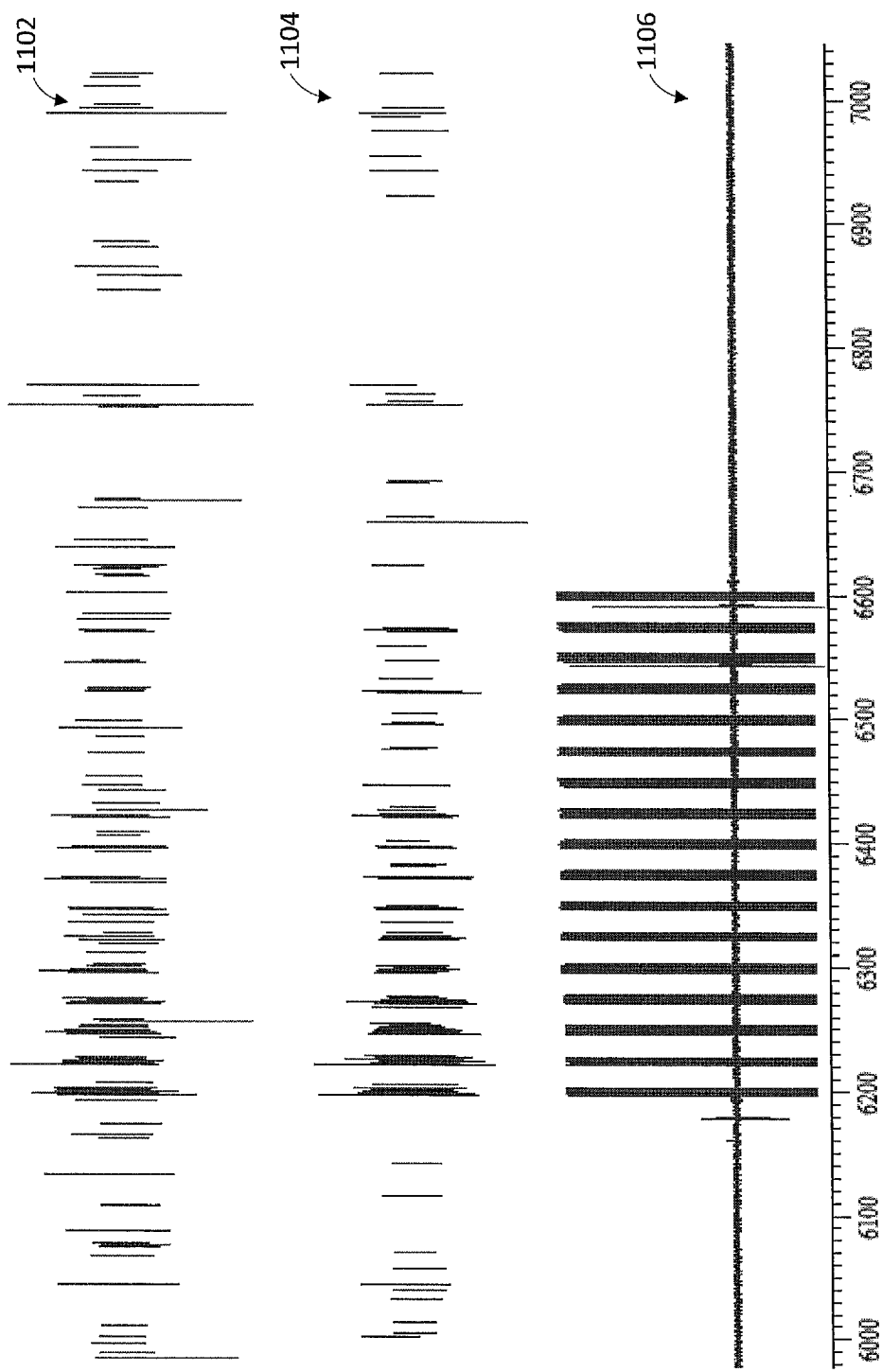
FIG. 11 is a diagram illustrating two cortical spike train traces during application of an exemplary microburst signal having 5 pulses per microburst, an amplitude of 0.75 mA, a frequency of 250 Hz, a pulse width of 500 microseconds, a interburst period of 0.5 seconds, an on time of 7 seconds, and an off time of 0.3 minutes.
Figure 12:
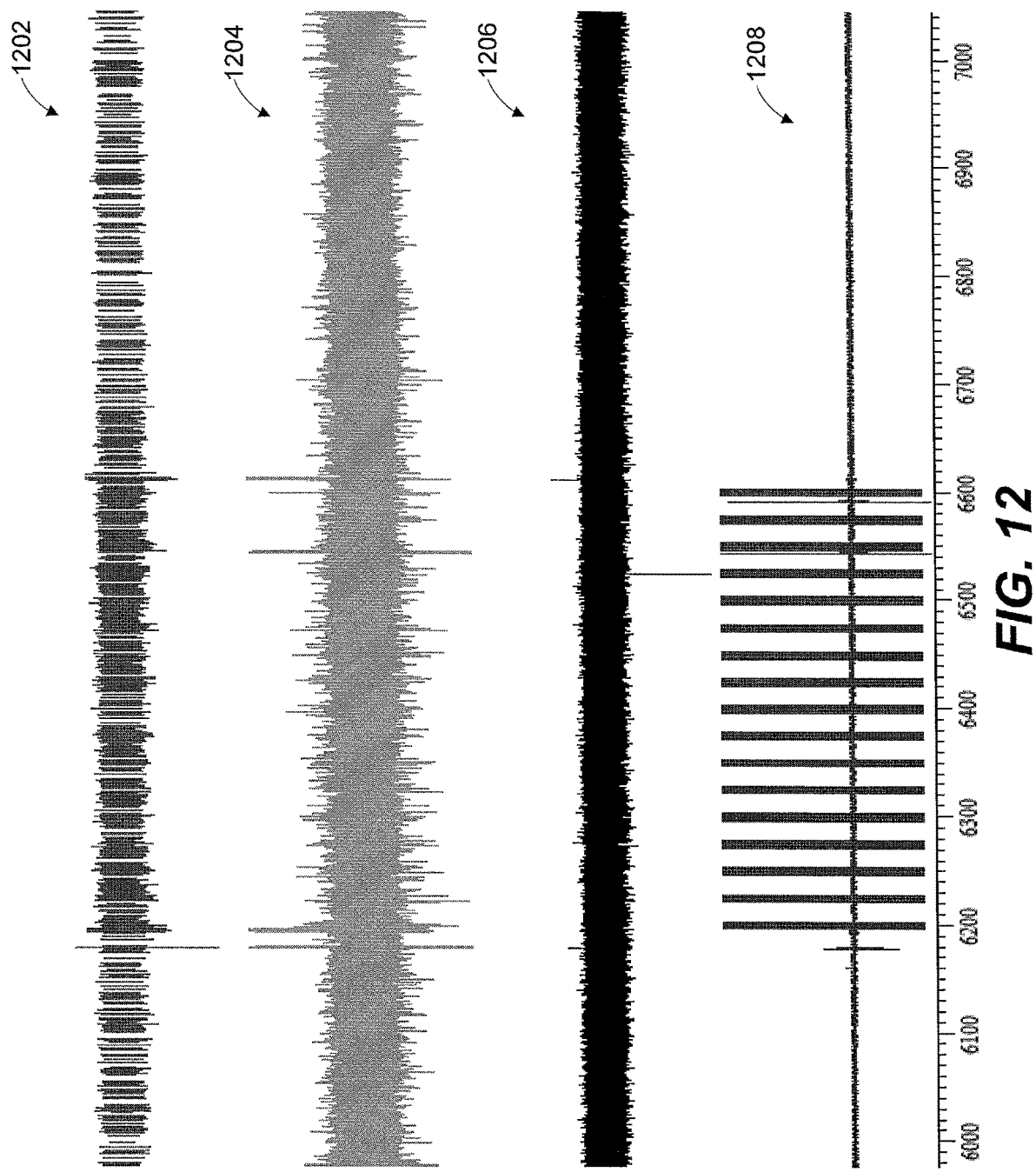
FIG. 12 is a diagram illustrating three NTS spike train traces during application of an exemplary microburst signal having 5 pulses per microburst, an amplitude of 0.75 mA, a frequency of 250 Hz, a pulse width of 500 microseconds, a interburst period of 0.5 seconds, an on time of 7 seconds, and an off time of 0.3 minutes.

FIGS. 9-12 illustrate exemplary body parameter data (e.g., spike train data) as spike train traces of one or more neurons during application of one or more microburst signals. The body parameter data in FIGS. 9-12 may be collected by the sensor data collection system 106 of FIG. 1 and provided to the IMD 104 of FIGS. 1 and 2. Spike train traces of 902 and 904 of FIG. 9 and spike train traces 1102 and 1104 of FIG. 11 illustrate spike train data as spike train traces of one or more neurons of a patient's parietal cortex during application of microburst signals 906 and 1106. To gather the spike train traces 902 and 904, micro burst signal 906 had the following stimulation parameters: 0.75 mA, 250 Hz, 500 microseconds pulsewidth, 5 pulses per microburst, 0.5 second interburst period, 30 seconds on-time, and 5 minutes off-time. To gather the spike train traces 1102 and 1104, microburst signal 1106 had the following parameters: 0.75 mA, 250 Hz, 500 microseconds pulsewidth, 5 pulses per microburst, 0.5 second interburst period, 7 seconds on-time, and 0.3 minutes off-time. Spike train traces 1002, 1004, and 1006 of FIG. 10 and 1202, 1204, and 1206 of FIG. 12 illustrate spike train data as spike train traces of one or more neurons of a patient's NTS during application of microburst signals 1008 and 1208, respectively. To gather the spike train traces 1002, 1004, and 1006, micro burst signal 1008 had the following parameters: 0.75 mA, 250 Hz, 500 microseconds pulsewidth, 5 pulses per microburst, 0.5 second interburst period, 30 seconds on-time, and 5 minutes off-time. To gather the spike train traces 1202, 1204, and 1206, microburst signal 1208 had the following parameters: 0.75 mA, 250 Hz, 500 microseconds pulsewidth, 5 pulses per microburst, 0.5 second interburst period, 7 seconds on-time, and 0.3 minutes off-time. As indicated by the spike train traces of FIGS. 9-12, application of microburst stimulation signals increases cortical activity without substantial NTS potentiation.

Figure 13:
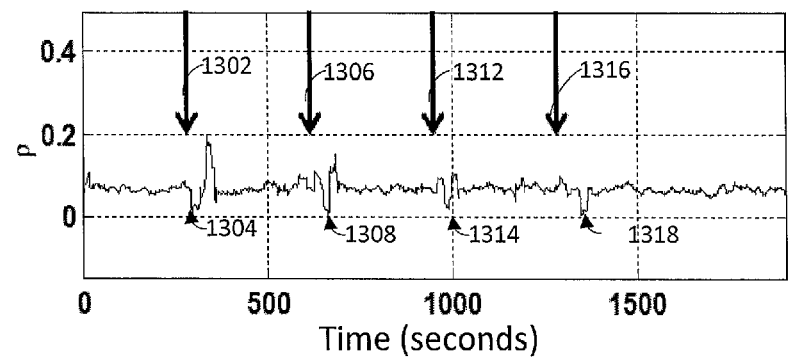
FIG. 13 is a plot of synchrony between neural activity of one or more regions of a patient's NTS and cortex during a period that includes application of one or more particular embodiments of non-micro burst signals to a cranial nerve of the patient.
Figure 15:
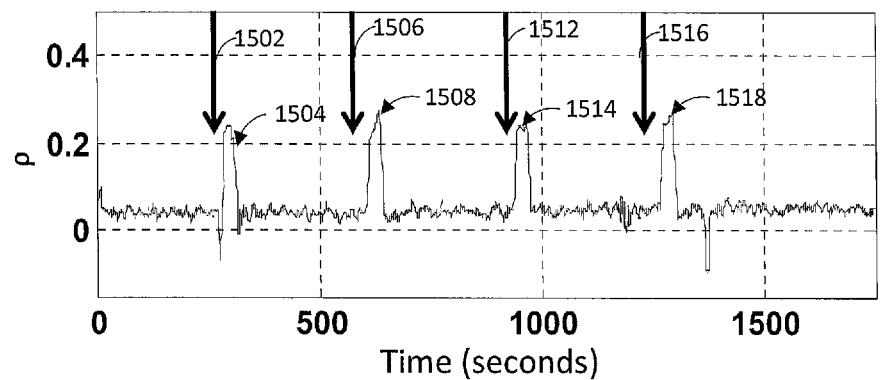
FIG. 15 is a plot of synchrony between neural activity of one or more regions of a patient's NTS and cortex during a period that includes application of one or more particular embodiments of micro burst signals to a cranial nerve of the patient.

FIGS. 13 and 15 are plots of one or more synchrony measurements. To generate FIG. 13, non-microburst signals were applied at times indicated by arrows 1302, 1306, 1312, and 1316. In FIG. 13, as indicated by troughs 1304, 1308, 1314, and 1318, synchrony appears to decrease in response to application of the non-micro burst signals. To generate FIG. 15, micro burst signals were applied at times indicated by arrows 1502, 1506, 1512, and 1516. In FIG. 15, as indicated by peaks 1504, 1508, 1514, and 1518, synchrony appears to increase in response to application of the micro burst signals.

Figure 14:
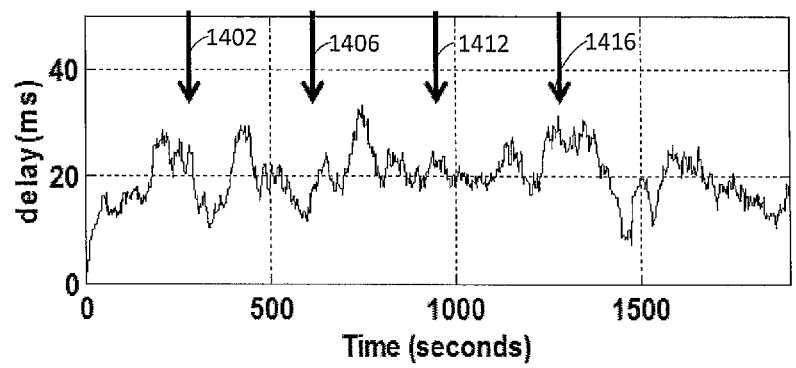
FIG. 14 is a plot of latency/delay of one or more regions of a patient's NTS and cortex during a period that includes application of one or more particular embodiments of non-microburst signals to a cranial nerve of the patient.
Figure 16:
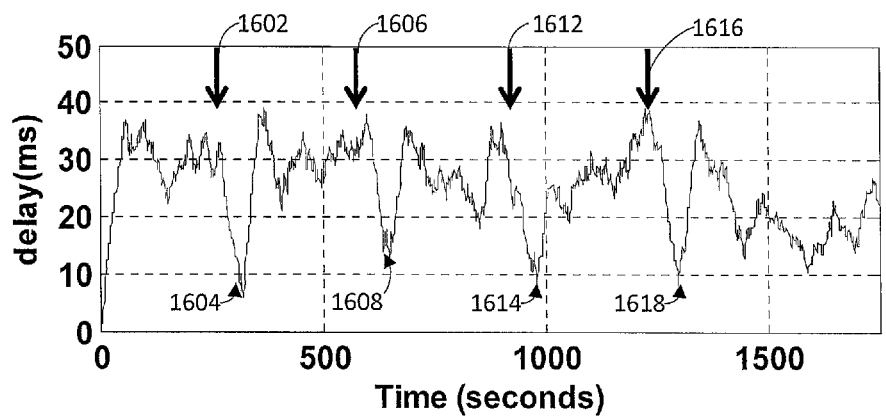
FIG. 16 is a plot of latency/delay of one or more regions of a patient's NTS and cortex during a period that includes application of one or more particular embodiments of microburst signals to a cranial nerve of the patient.

FIGS. 14 and 16 are plots of neuronal latency/delay between an NTS and cortex. To generate FIG. 14, non-microburst signals were applied at times indicated by arrows 1402, 1406, 1412, and 1416. In FIG. 14, latency/delay does not appear to consistently decrease in response to the non-microburst signals. To generate FIG. 16, microburst signals were applied at times indicated by arrows 1602, 1606, 1612, and 1616. In FIG. 16, as indicated by peaks 1604, 1608, 1614, and 1618, latency/delay appears to decrease in response to application of the microburst signals.

As illustrated in FIGS. 3-12, NTS and cortical regions respond differently to application of micro burst stimulation and non-micro burst stimulation. Neural activity in cortical regions can be increased by application of microburst signals. Activity in NTS regions can be increased using non-microburst signals; however, non-microburst signals do not appear to activate cortical regions. In contrast to application of non-microburst signals, synchrony between one or more regions of an NTS and one or more regions of a cortex may be substantially increased by application of micro burst signals.

Figure 17:
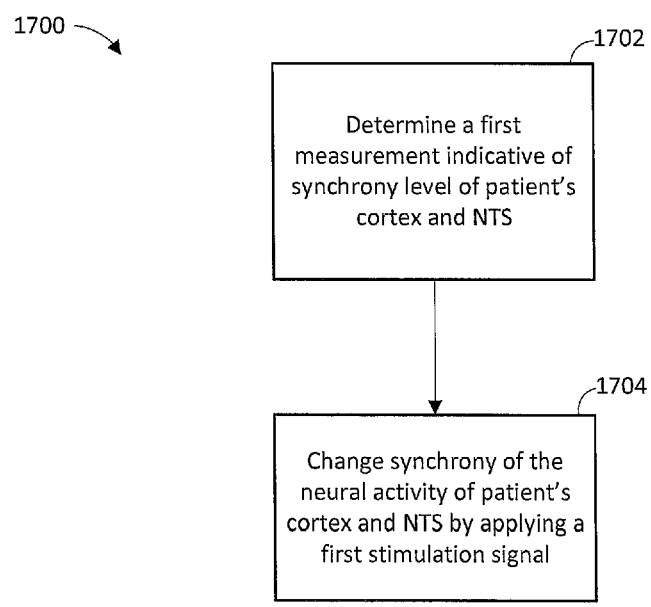
FIG. 17 is a flow chart of a first particular embodiment of a method of operation of an implantable medical device that uses CNS to change a synchrony between neural activity of one or more regions of a patient's autonomic nervous system and one or more regions of the patient's central nervous system.

FIG. 17 is a flow chart of a particular embodiment of a method of treating seizure disorders using an implantable medical device. For example, the method 1700 may be performed using the IMD 104 of FIG. 1 in conjunction with the sensor data collection system 106 of FIG. 1.

The method 1700 includes determining a synchrony measurement (e.g., "first synchrony measurement") of the patient, at 1702, for a first window of body parameter data. The window of body parameter data may correspond to a particular time span during which body parameter data is gathered. Alternatively, the window of body parameter data may be defined based on a parameter other than time, such as one or more stimulation parameters. For example, a window of body parameter data may begin at a start of an on-time period of a stimulation signal and may end at a start of an off-time period of a stimulation signal. The first synchrony measurement may be determined by the processor 110 of the IMD 104 of FIG. 1 using body parameter data from the sensor data collection system 106 as described above. The first synchrony measurement may be in the form of a rate of change of a value indicative of synchrony between neural activity of one or more regions of the patient's autonomic nervous system and one or more regions of the patient's central nervous system. The first synchrony measurement may also, or in the alternative, be in the form of a measure of latency of communication between one or more regions of the patient's autonomic nervous system and one or more regions of the patient's central nervous system. The first synchrony measurement may also, or in the alternative, be determined using measurements collected by the sensor data collection system 106 of neural activity at one or more regions of the patient's autonomic nervous system and one or more regions of the patient's central nervous system. The first synchrony measurement may also be determined using body parameter data collected by the sensor data collection system 106 from one or more areas of the patient's body other than the patient's brain (e.g., heart rate variability data, heart rate morphology data, or a combination thereof).

The method 1700 may further include changing the synchrony level of neural activity of one or more regions of one or more regions of the patient's autonomic nervous system and one or more regions of the patient's central nervous system by applying a first stimulation signal based on the first synchrony measurement, at 1704. In some embodiments, application of the first stimulation signal may be controlled and/or performed using the TDU 116 of FIG. 1. In some embodiments, the first stimulation signal may be a micro burst signal (e.g., 906, 1008, 1106, 1208 of FIGS. 9-12). In some embodiments, when applied to the patient, the first stimulation signal may increase a synchrony between neural activity of one or more regions of one or more regions of the patient's autonomic nervous system and one or more regions of the patient's central nervous system. In some embodiments, the first stimulation signal may be a non-microburst signal.

The first stimulation signal may be applied based on a determination that the first synchrony measurement indicates a seizure state (e.g., onset and/or imminent onset of a seizure) as described above. In some embodiments, the processor 110 determines whether the synchrony measurement indicates a seizure state (e.g., by determining whether the first synchrony measurement satisfies a threshold synchrony value as described above).

Synchrony between neural activity of one or more regions of a patient's autonomic nervous system and one or more regions of a patient's central nervous system may decrease at a relatively high rate and/or be at a substantially low level (relative to a non-seizure state) during the seizure state; the rate of decrease and/or relatively low level may be indicative of the seizure state (e.g., an ongoing seizure and/or onset or imminent onset of a seizure). Thus, the method of FIG. 17 may include changing (e.g., increasing) a synchrony between one or more regions of the patient's autonomic nervous system and one or more regions of the patient's central nervous system by applying one or more stimulation signals (e.g., microburst signals).

In some embodiments, changing the synchrony between neural activity of one or more regions of the patient's autonomic nervous system and one or more regions of the patient's central nervous system based on the first synchrony measurement includes increasing the synchrony between neural activity of one or more regions of the patient's autonomic nervous system and one or more regions of the patient's central nervous system by applying one or more micro burst signals to a cranial nerve of the patient. For example, one or more micro burst signals (e.g., 906, 1008, 1106, 1208 in FIGS. 9-12) may be applied. As illustrated in FIG. 15, application of one or more microburst signals to a patient's cranial nerve may increase synchrony between neural activity of one or more regions of a patient's NTS and one or more regions of the patient's cortex. In FIG. 15, microburst signals were applied at times indicated by arrows 1502, 1506, 1512, and 1516. As indicated by peaks 1504, 1508, 1514, and 1518, synchrony between one or more regions of the patient's autonomic nervous system (e.g. NTS) and the patient's central nervous system (e.g. cortex) was increased by application of one or more microburst signals.

Figure 18:
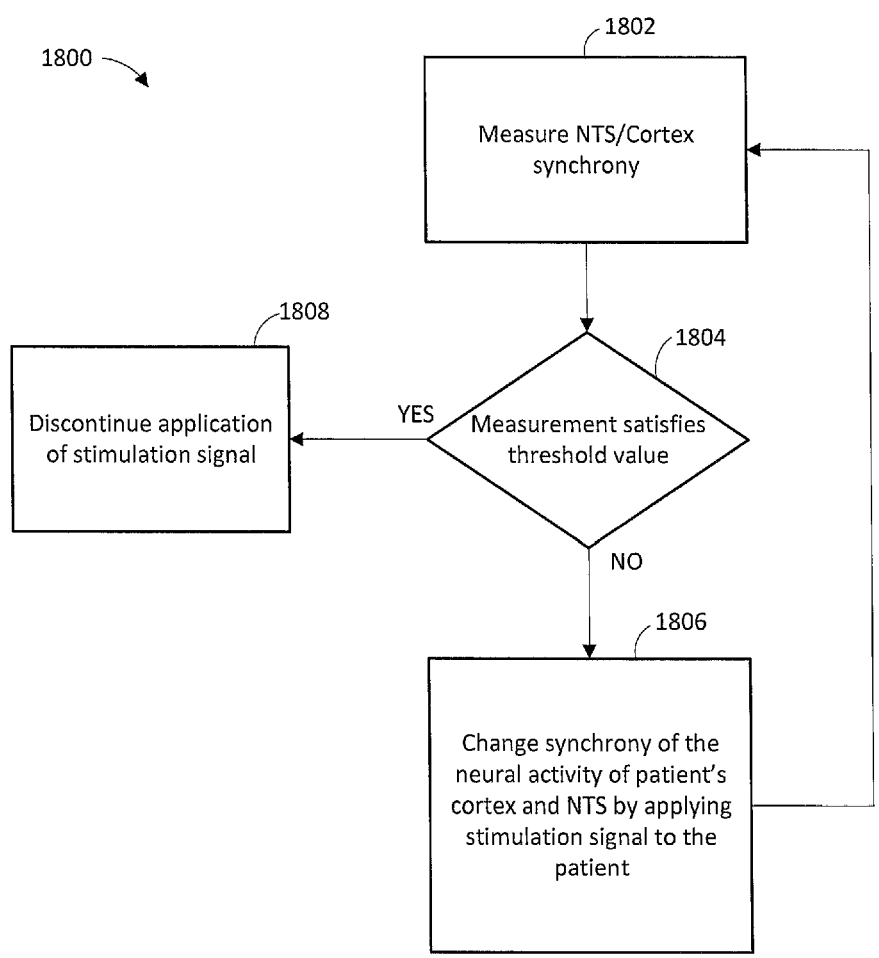
FIG. 18 is a flow chart of a particular embodiment of a method of operation of an implantable medical device that applies one or more stimulation signals to a patient's cranial nerve until a measurement of synchrony between one or more regions of the patient's autonomic nervous system and one or more regions of the patient's central nervous system satisfies a threshold value.

FIG. 18 is a flow chart of a particular embodiment of a method 1800 of treating seizure disorders by changing a synchrony between neural activity of a patient using an implantable medical device to apply one or more stimulation signals until a synchrony between neural activity of one or more regions of the patient's autonomic nervous system and one or more regions of the patient's central nervous system satisfies a threshold value. For example, the method 1800 may be performed using the IMD 104 in conjunction with the sensor data collection system 106 of FIG. 1.

The method 1800 may include determining a synchrony measurement (e.g., a "first synchrony measurement") of the patient, at 1802, for a first window of body parameter data (e.g., a "first window"). The first window may correspond to a particular time span during which body parameter data is gathered. Alternatively, the first window may be defined based on a parameter other than time, such as one or more stimulation parameters. For example, a first window may begin at a start of an on-time period of a stimulation signal and may end at a start of an off-time period of a stimulation signal. The first synchrony measurement may be determined by the processor 110 of the IMD 104 of FIG. 1 using body parameter data from the sensor data collection system 106 as described above.

The method 1800 may further include determining whether the first synchrony measurement satisfies a threshold value, at 1804. In some embodiments, the processor 110 determines whether the first synchrony measurement satisfies a threshold value. The threshold value may be a value indicative of a threshold level of synchrony (e.g., a "threshold synchrony value") between neural activity of one or more regions of the patient's autonomic nervous system and one or more regions of the patient's central nervous system. In some embodiments, the threshold synchrony value may be a value indicative of a threshold rate of change of synchrony between neural activity of one or more regions of the patient's autonomic nervous system and one or more regions of the patient's central nervous system.

In some embodiments, the threshold synchrony value may be indicative of a non-seizure state (e.g., seizure termination) as described above. For example, in embodiments in which the threshold synchrony value is indicative of a non-seizure state (e.g., seizure termination), the method may include applying one or more microburst signals until the first synchrony measurement satisfies the threshold synchrony value, thereby indicating that the patient is no longer experiencing a seizure. In response to determining that the first synchrony measurement satisfies the threshold synchrony value, micro burst stimulation may be discontinued (e.g. in favor of application of non-microburst stimulation). Alternatively, or in addition, the method may include applying one or more non-microburst signals until the first synchrony measurement satisfies the threshold synchrony value, thereby indicating that the patient is no longer experiencing a seizure. In response to determining that the first synchrony measurement satisfies the threshold, non-micro burst stimulation may be discontinued (e.g. in favor of application of microburst stimulation). In some embodiments, the threshold synchrony value may be (e.g., selected to be) a value indicative of a threshold rate of change of synchrony associated with seizure termination, and the first synchrony measurement may be in the form of a rate of change of synchrony, as described above.

In some embodiments, the threshold synchrony value may be indicative of a seizure state (e.g., onset of a seizure) as described above. For example, in embodiments in which the threshold synchrony value is indicative of a seizure state (e.g., onset of a seizure), the method may include applying one or more non-microburst signals until the synchrony measurement satisfies the threshold synchrony value, thereby indicating onset of a seizure. In response to determining that the synchrony measurement satisfies the threshold synchrony value, non-microburst stimulation may be discontinued (e.g. in favor of application of micro burst stimulation). Alternatively, or in addition, the method may include applying one or more microburst signals until the synchrony measurement satisfies the threshold synchrony value, thereby indicating seizure onset. In response to determining that the synchrony measurement satisfies the threshold synchrony value, micro burst stimulation may be discontinued (e.g. in favor of application of non-microburst stimulation). In some embodiments, the threshold synchrony value may be (e.g., selected to be) a value indicative of a threshold rate of change of synchrony associated with seizure onset, and the first synchrony measurement may be in the form of a rate of change of synchrony, as described above. A threshold rate of change of synchrony value may be selected such that the rate of change indicates onset of a seizure.

A threshold rate of change of synchrony value may alternatively be selected such that the rate of change indicates that the stimulation is becoming ineffective (e.g., when the rate of change of a synchrony measurement satisfies the threshold rate of change value, the current stimulation parameters are sufficiently ineffective to produce desired response and should be adjusted). For example, micro burst stimulation may be applied to a patient at onset of a seizure event as described above. During the seizure event, at 1802, a synchrony measurement (in the form of a rate of change of synchrony) of the patient may be determined. The synchrony measurement may be compared to the threshold rate of change of synchrony. When it is determined that the synchrony measurement satisfies the threshold rate of change value, microburst stimulation may be discontinued in favor of non-microburst stimulation during the seizure event. Alternatively, when it is determined that the synchrony measurement satisfies the threshold rate of change value, a microburst stimulation parameter may be adjusted in response to determining that the synchrony measurement satisfies the threshold rate of change value.

Any one or more synchrony measurements, threshold values, and stimulation signals of a particular iteration of 1800 may be different than any one or more synchrony measurements, threshold values, and stimulation signals of a subsequent iteration of 1800. For example, during a first iteration of 1800, a first synchrony measurement may be determined, at 1802, based on a first window of body parameter data, and a first stimulation signal (e.g., a first micro burst signal) may be applied at 1806. During a subsequent iteration of 1800 (e.g., when the first synchrony measurement does not satisfy the threshold synchrony value, at 1804), a second synchrony measurement may be determined based on a second window of body parameter data and a second stimulation signal (e.g., a "second micro burst signal") may be applied, at 1806. The second window may or may not include different body parameter data than the first window. The second stimulation signal (e.g., the second micro burst signal) may or may not include one or more different stimulation parameters than the first stimulation signal (e.g., the first microburst signal). For example, the second synchrony measurement may indicate that the first stimulation signal did not produce a satisfactory synchrony response (e.g., did not sufficiently increase the synchrony). To increase the efficacy of the stimulation therapy, one or more stimulation signal parameters (e.g., amplitude, microburst duration, etc.) may be adjusted such that the second stimulation signal has different parameters (e.g., greater amplitude) than the first stimulation signal.

Figure 19:
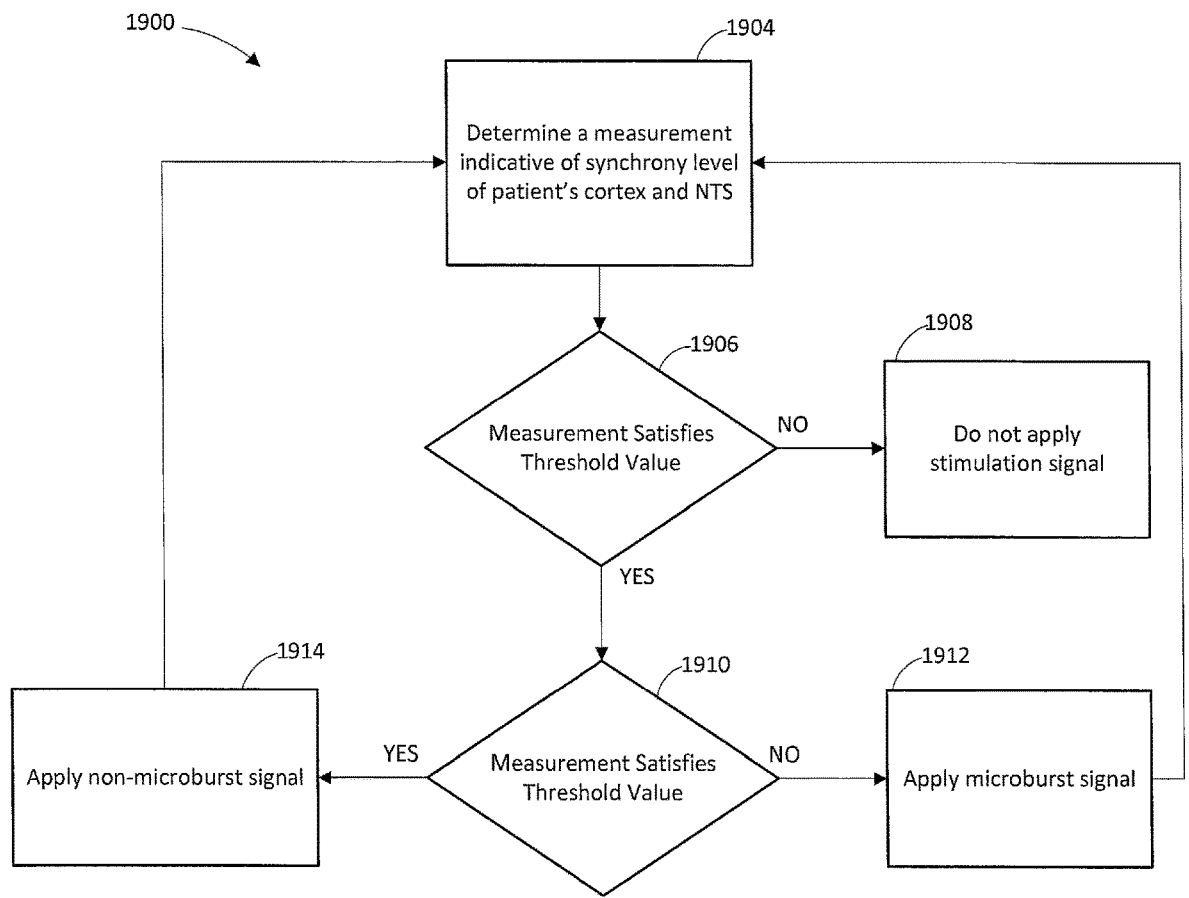
FIG. 19 is a flow chart of a particular embodiment of a method of operation of an implantable medical device that applies one or more microburst signals and/or one or more non-microburst signal based on whether one or more measurements of synchrony between one or more regions of the patient's autonomic nervous system and one or more regions of the patient's central nervous system satisfies a threshold value until one or more synchrony measurements satisfies a threshold value.

FIG. 19 is a flow chart of a particular method of treating seizures that includes evaluating one or more synchrony measurements of the patient to determine occurrence of a seizure, and evaluating the same, or different, one or more of the patient's synchrony measurements to determine whether to apply a microburst or non-microburst signal when a seizure is determined to be occurring. For example, the method of FIG. 19 may be performed using the IMD 104 in conjunction with the sensor data collection system 106 of FIG. 1.

The method 1900 may include determining a synchrony measurement (e.g., a "first synchrony measurement"), at 1904, for a first window of body parameter data. The first window of body parameter data may correspond to a particular time span during which body parameter data of the patient is gathered. Alternatively, the first window of body parameter data may be defined based on a parameter other than time, such as one or more stimulation parameters. For example, a window of body parameter data may begin at a start of an on-time period of a stimulation signal and may end at a start of an off-time period of a stimulation signal. The first synchrony measurement may be determined by the processor 110 of the IMD 104 in FIG. 1 using body parameter data from the sensor data collection system 106 as described above.

The method 1900 may further include determining whether the first synchrony measurement satisfies a first threshold value, at 1906. In some embodiments, the first threshold value may be a threshold synchrony value (e.g., a "first threshold synchrony value") associated with a seizure state (e.g., an ongoing seizure and/or onset of a seizure) or a non-seizure state (e.g., seizure termination), as described above. When the first threshold synchrony value is associated with a seizure state, the first synchrony measurement may satisfy the first threshold synchrony value at onset of a seizure as described above. When the first threshold synchrony value is associated with a non-seizure state, the first synchrony measurement may satisfy may the threshold synchrony value at termination of a seizure as described above.

The method 1900 may further include determining whether the first synchrony measurement satisfies a second threshold value, at 1910, when the first synchrony measurement satisfies the first threshold value, at 1906. In some embodiments, the processor 110 of FIG. 1 determines whether the first synchrony measurement satisfies the second threshold value, at 1910. The second threshold value may be a threshold synchrony value (e.g., a "second threshold synchrony value"). The first threshold value may be the same as or different than the second threshold value. The first and second threshold values used during a first iteration of the method of FIG. 19 may be the same as or different than the corresponding first and second threshold values used in one or more subsequent iterations. For example, in some embodiments, a first threshold value of a first iteration of the method 1900 may be selected to be indicative of seizure onset as described above, while a first threshold value of a subsequent iteration of 1900 may be selected to be indicative of seizure termination as described above, where the first threshold value indicative of a seizure onset is different than the first threshold value indicative of seizure termination.

As a further example, a second threshold value of a first iteration of the method 1900 and a subsequent iteration may be in the form of a threshold rate of change of synchrony as described above. The second threshold value of the first iteration may be different than the second threshold value of the subsequent iteration. For example, the second threshold value of the subsequent iteration may be adjusted to be greater than or less than the second threshold value of the first iteration because the rate of change of synchrony may be expected to decrease as the patient builds a tolerance to stimulation therapy.

The method 1900 may further include applying a microburst signal (e.g., 906, 1008, 1106, 1208 of FIGS. 9-12), at 1912, when the first synchrony measurement does not satisfy the second threshold value. In some embodiments, application of the microburst signal may be controlled and/or performed using TDU 116 of FIG. 1. In some embodiments, when applied to the patient, the microburst signal may increase a synchrony between neural activity of one or more regions of the patient's autonomic nervous system and one or more regions of the patient's central nervous system.

The method 1900 may further include applying a non-microburst signal (e.g., 306, 406, 506, 606, 706, 806 of FIGS. 3-8), at 1914, when the first synchrony measurement satisfies the threshold value. In some embodiments, application of the non-micro burst signal may increase a synchrony between neural activity of one or more regions of the patient's autonomic nervous system and one or more regions of the patient's central nervous system.

The method 1900 returns to 1904 to perform a subsequent iteration of the method of FIG. 19 as described above.

Figure 20:
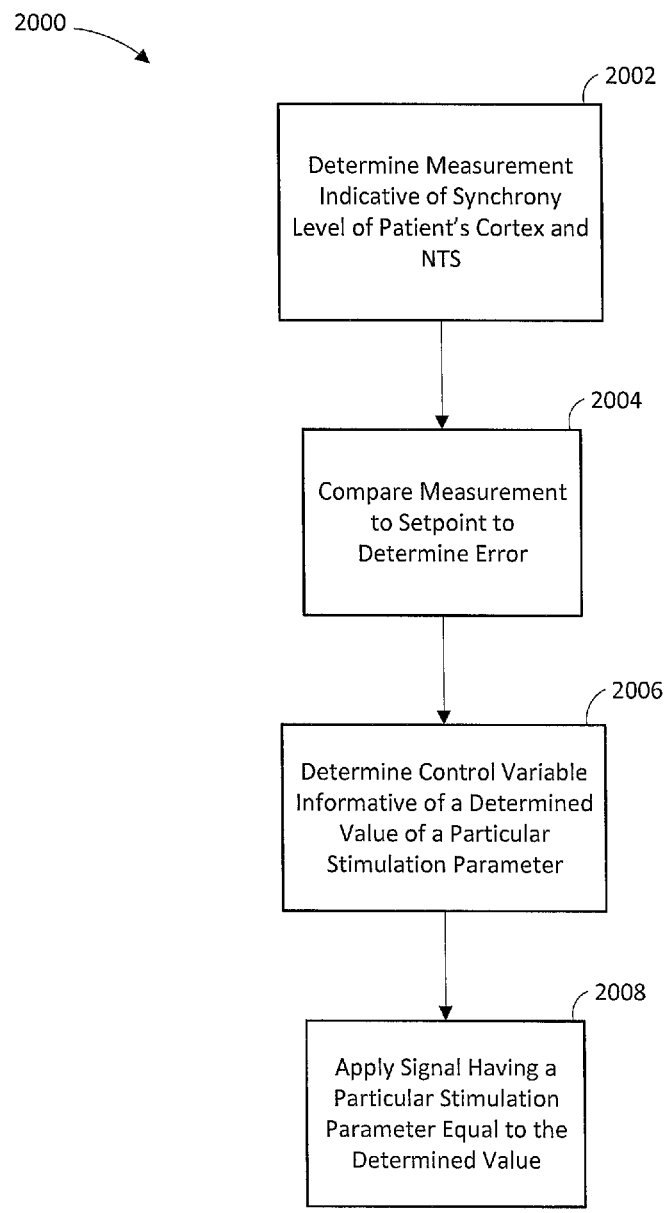
FIG. 20 is a flow chart of a particular embodiment of a method of operation of an implantable medical device that applies a stimulation signal to a patient's cranial nerve based on one or more parameters determined using a controller of a feedback control loop.

FIG. 20 is a flow chart of a particular method of treating a seizure disorder by determining a stimulation parameter of a stimulation signal. For example, the method of FIG. 20 may be performed using the controller 123 of FIG. 1. The controller 123 may be a PI controller, a PID controller, or some other controller configured to perform operations as described with reference to FIG. 20.

The method 2000 may include determining a synchrony measurement (e.g., a "second synchrony measurement"), at 2002, for a window (e.g., a "second window") of body parameter data. The second window of body parameter data may be collected by the sensor data collection system 106 after application of a first stimulation signal is initiated (e.g., the second window begins after application of the first stimulation signal is initiated). The second window may correspond to a particular time span during which body parameter data is gathered. Alternatively, the second window may be defined based on a parameter other than time, such as one or more stimulation parameters. For example, the second window of body parameter data may begin at a start of an on-time period of the stimulation signal and may end at a start of an off-time period of the first stimulation signal.

The method 2000 further includes processing, at 2004 (e.g., using the processor 110 of FIG. 1), the second synchrony measurement to determine an error between the second synchrony measurement and a setpoint. In some embodiments, the setpoint is a predicted value of a response of the patient to application of the first stimulation signal and is predicted based on a model. In some embodiments, the setpoint may be a threshold synchrony value indicative of a baseline synchrony level of the patient (e.g., a synchrony level of the patient when the patient is not experiencing a seizure). At least one stimulation parameter may be determined (e.g., using the processor 110 of FIG. 1) based on a control variable value determined using the error, at 2006. For example, in some embodiments, an amplitude value of a stimulation signal may be determined based on the error.

In other embodiments, the at least one stimulation parameter may include a stimulation parameter other than amplitude.

The method 2000 further includes applying, at 2008, a second stimulation signal to one or more cranial nerves of the patient based on the at least one stimulation parameter (e.g., using the TDU 116 of FIG. 1). The second stimulation signal may be a microburst signal (e.g., 906, 1008, 1106, 1208 in FIGS. 9-12). For example, in some embodiments, where at least one stimulation parameter determined, at 2006, is an amplitude of a stimulation signal, the second stimulation signal may be set to have an amplitude equal to, or based on, the amplitude value determined, at 2006.

Figure 21:
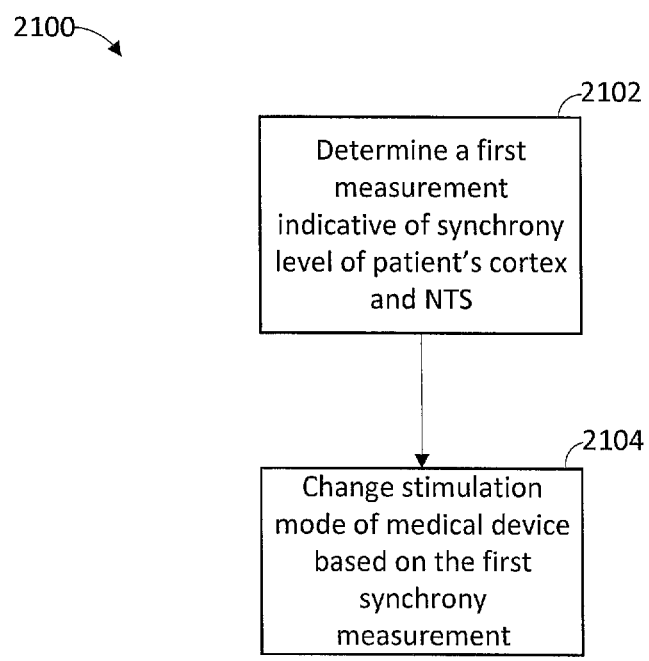
FIG. 21 is a flow chart of a particular embodiment of a method of operation of an implantable medical device that changes a stimulation mode of the implantable medical device based on a measurement of a synchrony between one or more regions of a patient's autonomic nervous system and one or more regions of the patient's central nervous system.

FIG. 21 is a flow chart of a particular embodiment of a method of treating seizure disorders using an implantable medical device (e.g., the IMD 104 of FIG. 1). The method 2100 includes changing a stimulation mode of the implantable medical device based on a measurement of synchrony between one or more regions of a patient's autonomic nervous system and one or more regions of the patient's central nervous system. For example, the method 2100 may be performed using the IMD 104 in conjunction with the sensor data collection system 106 of FIG. 1. The method includes determining a synchrony measurement of the patient, at 2102, for a window (e.g., a "first window") of body parameter data as described above. The window of body parameter data may correspond to a particular time span during which body parameter data is gathered. Alternatively, the window of body parameter data may be defined based on a parameter other than time, such as one or more stimulation parameters. For example, a window of body parameter data may begin at a start of an on-time period of a stimulation signal and may end at a start of an off-time period of a stimulation signal. The synchrony measurement may be determined by the processor 110 of the IMD 104 in FIG. 1 using body parameter data from the sensor data collection system 106 as described above.

The method 2100 further includes changing a stimulation mode of the IMD 104 from a first stimulation mode (e.g., microburst or non-microburst stimulation mode) to a second stimulation mode (e.g., micro burst or non-micro burst stimulation mode) based on the first synchrony measurement, at 2104. In the microburst stimulation mode, the IMD 104 (e.g., using the TDU 116) is configured to apply one or more microburst signals to a cranial nerve of the patient. In the non-microburst stimulation mode, the IMD 104 (e.g., using the TDU 116) is configured to apply one or more non-micro burst signals to a cranial nerve of the patient.

The IMD 104 may change its stimulation mode from a first stimulation mode (e.g., micro burst or non-micro burst) to a second stimulation mode (e.g., micro burst or non-micro burst) based on a determination by the processor 110 that the synchrony measurement satisfies a threshold synchrony value.

In some embodiments, the threshold synchrony value may be indicative of a seizure state as described above. The IMD 104 of FIG. 1 may change its stimulation mode in response to determining that the synchrony measurement satisfies the threshold synchrony value indicative of the seizure state.

For example, the IMD 104 may be operating, or set to operate, in a non-microburst stimulation mode prior to determining that the first synchrony measurement satisfies a threshold synchrony value indicative of the seizure state (e.g., seizure onset). The IMD 104 may change its stimulation mode from non-microburst stimulation mode to microburst stimulation mode in response to the processor 110 determining that the first synchrony measurement indicates that synchrony between neural activity of one or more regions of the patient's autonomic nervous system and one or more regions of the patient's central nervous system satisfies (e.g., is below, is decreasing at a rate greater than, or both) a threshold synchrony value indicative of onset of a seizure.

As another example, the IMD 104 may be operating, or set to operate, in a microburst stimulation mode prior to determining that the first synchrony measurement satisfies a threshold synchrony value indicative of onset of the seizure state (e.g., seizure onset). The IMD 104 may change its stimulation mode from microburst stimulation mode to non-microburst stimulation mode in response to determining that the synchrony measurement satisfies the threshold synchrony value. For example, the IMD 104 may change its stimulation mode from micro burst stimulation mode to non-micro burst stimulation mode in response to the processor 110 determining that the first synchrony measurement indicates that synchrony between neural activity of one or more regions of the patient's autonomic nervous system and one or more regions of the patient's central nervous system satisfies (e.g., is below, is decreasing at a rate greater than, or both) the threshold synchrony value.

In some embodiments, the threshold synchrony value may be indicative of a non-seizure state as described above. The IMD 104 may change its stimulation mode in response to determining that the synchrony measurement satisfies the threshold synchrony value indicative of the non-seizure state.

For example, the IMD 104 may be operating, or set to operate, m a microburst stimulation mode prior to determining that the first synchrony measurement satisfies a threshold synchrony value indicative of a non-seizure state (e.g., seizure termination). The IMD 104 may change its stimulation mode from microburst stimulation mode to non-microburst stimulation mode in response to the processor 110 determining that the first synchrony measurement indicates that synchrony between neural activity of one or more regions of the patient's autonomic nervous system and one or more regions of the patient's central nervous system satisfies (e.g., is above, is increasing at a rate greater than, or both) a threshold synchrony value indicative of termination of a seizure.

As another example, the IMD 104 may be operating, or set to operate, m a non-microburst stimulation mode prior to determining that the first synchrony measurement satisfies a threshold synchrony value indicative of a non-seizure state (e.g., seizure termination). The IMD 104 may change its stimulation mode from non-microburst stimulation mode to microburst stimulation mode in response to the processor 110 determining that the first synchrony measurement indicates that synchrony between neural activity of one or more regions of the patient's autonomic nervous system and one or more regions of the patient's central nervous system satisfies (e.g., is above, is increasing at a rate greater than, or both) a threshold synchrony value indicative of termination of a seizure.

Figure 22:
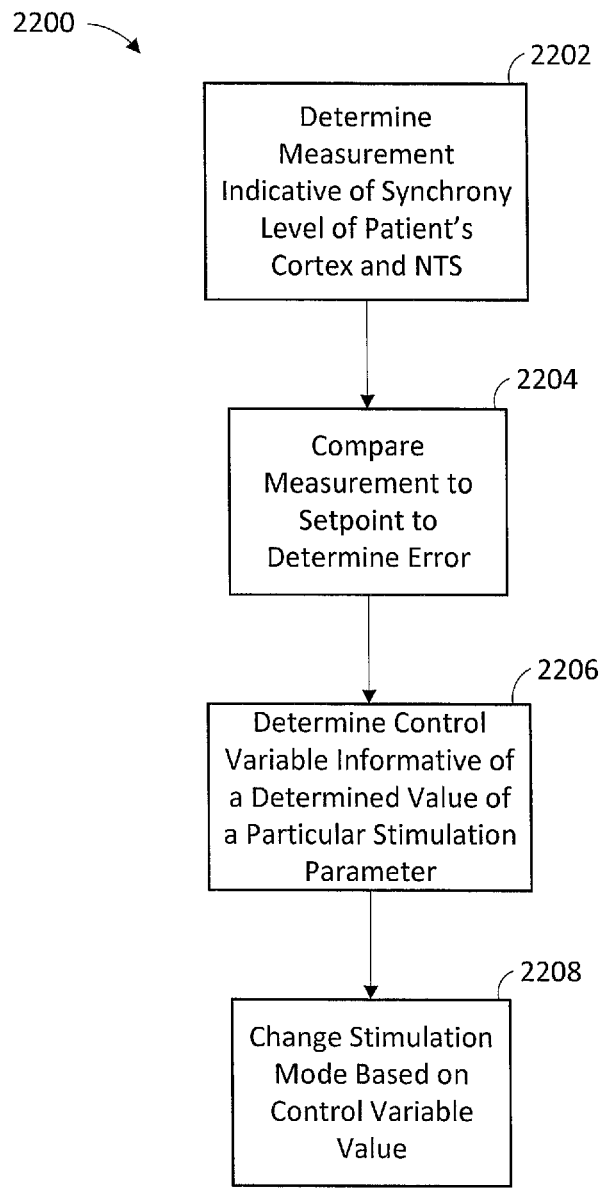
FIG. 22 is a flow chart of a particular embodiment of a method of operation of an implantable medical device that changes a stimulation mode of the implantable medical device based on a measurement of synchrony between one or more regions of a patient's autonomic nervous system and one or more regions of the patient's central nervous system using a controller of a feedback control loop.

FIG. 22 is a flow chart of a particular method of treating a seizure disorder. The method of FIG. 22 includes changing a stimulation mode of a medical device using a controller. The controller may be a PI controller, a PID, or some other controller configured to perform operations described with reference to FIG. 22.

The method 2200 may include determining a synchrony measurement (e.g., a "second synchrony measurement"), at 2202, for a window (e.g., a "second window") of body parameter data. The second window of body parameter data collected by the sensor data collection system 106 after application of a first stimulation signal is initiated (e.g., the second window begins after application of the first signal is initiated). The second window may correspond to a particular time span during which body parameter data is gathered. Alternatively, the second window may be defined based on a parameter other than time, such as one or more stimulation parameters. For example, the second window of body parameter data may begin at a start of an on-time period of the stimulation signal and may end at a start of an off-time period of the first stimulation signal.

The method 2200 further includes processing the second synchrony measurement, at 2204, (e.g., using the processor 110 of FIG. 1) to determine an error between the second synchrony measurement and a setpoint. In some embodiments, the setpoint is a predicted value of a response of the patient to application of the first stimulation signal and is predicted based on a model. In some embodiments, the setpoint may be a value indicative of a baseline synchrony level of the patient.

The method 2200 further includes determining a control variable value indicative of whether to change a stimulation mode of the IMD 104, at 2206. For example, the control variable value may be a value of a particular stimulation parameter corresponding to a particular stimulation mode different than the stimulation mode in which the IMD 104 is set or operating. For example, the IMD 104 may be operating, or set to operate, in a non-microburst stimulation mode when the second synchrony measurement is determined, at 2202. A control variable value in the form of a stimulation parameter value (e.g., micro burst duration) corresponding to operation in microburst stimulation mode may be determined, at 2206. The control variable value may be a value indicative of a seizure state (e.g., ongoing seizure, seizure onset, and/or imminent seizure onset) or a non-seizure state (e.g., termination of a seizure and/or imminent seizure termination). For example, the IMD 104 may be operating or set in a non-microburst stimulation mode when the second synchrony measurement is determined, at 2202. A control variable value indicating a seizure state or a non-seizure state may be determined, at 2206.

The method 2200 further includes changing the stimulation mode of the IMD 104 based on the control variable value, at 2206. For example, the IMD 104 may be operating, or set to operate, in a non-micro burst stimulation mode. A control value indicative of a seizure state (e.g., onset of a seizure) may be determined, at 2206. Based on determining the control variable value indicative of onset of the seizure, the IMD 104 may change its stimulation mode to a micro burst stimulation mode (e.g., may cause the TDU 116 to apply microburst stimulation). As another example, the IMD 104 may be operating, or set to operate, in a micro burst stimulation mode. A control variable value indicative of a non-seizure state (e.g., seizure termination) may be determined, at 2206. Based on determining the control variable value indicative of termination of the seizure, the IMD 104 may change its stimulation mode to a non-microburst stimulation mode (e.g., the IMD 104 may instruct the TDU 116 to apply non-microburst stimulation).

Figure 23:
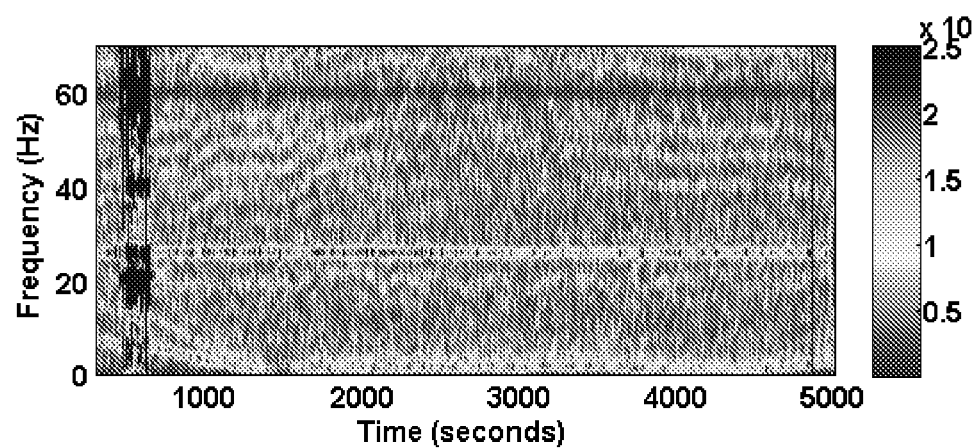
FIG. 23 is a power spectrum plot of a neuronal activity of a patient's autonomic nervous system.
Figure 24:
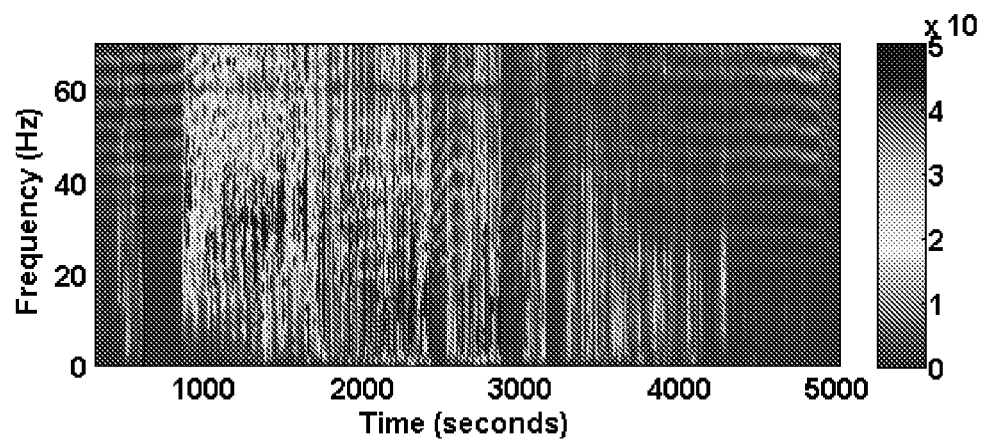
FIG. 24 is a power spectrum plot of a neuronal activity of a patient's central nervous system.
Figure 25:
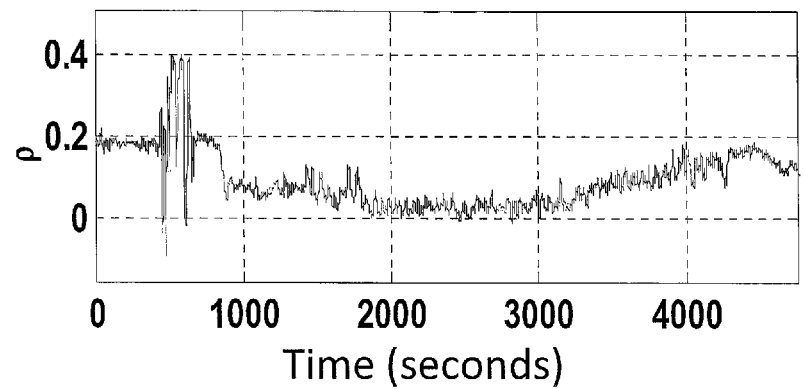
FIG. 25 is a plot of synchrony between neural activity of an autonomic nervous system and a central nervous system.
Figure 26:
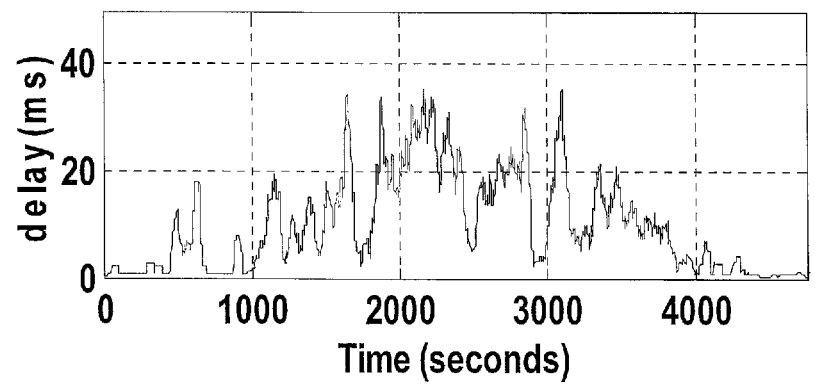
FIG. 26 is a plot of latency/delay between an autonomic nervous system and a central nervous system.

FIGS. 23 and 24 represent body parameter data such as measurements indicative of neural activity of one or more regions of a subject's NTS and cortex, respectively. FIG. 25 illustrates synchrony measurement determined based on the body parameter data illustrated in FIGS. 23 and 24. FIG. 26 illustrates a synchrony measurement in the form of a plot of latency between the subject's NTS and one or more regions of the subject's cortex. To generate FIGS. 23-26, a seizure was induced at 600 seconds. As illustrated in FIGS. 25 and 26, a synchrony between neural activity of the measured regions of the NTS and cortex decreases during a seizure. Thus, a treatment that increases synchrony between one or more regions of the patient's autonomic nervous system and one or more regions of the patient's central nervous system may be useful in treating seizure disorders.

Figure 27:
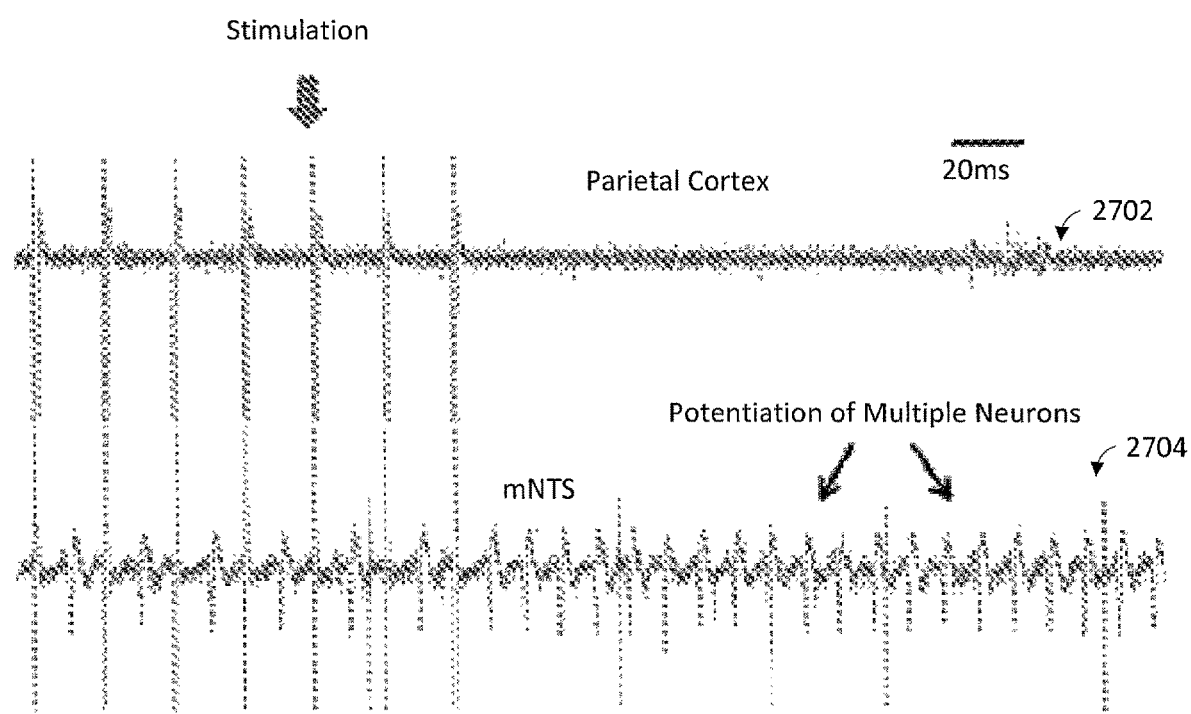
FIG. 27 shows plots of action potentials in a subject's autonomic nervous system and central nervous system during application of particular non-micro burst signals.
Figure 28:
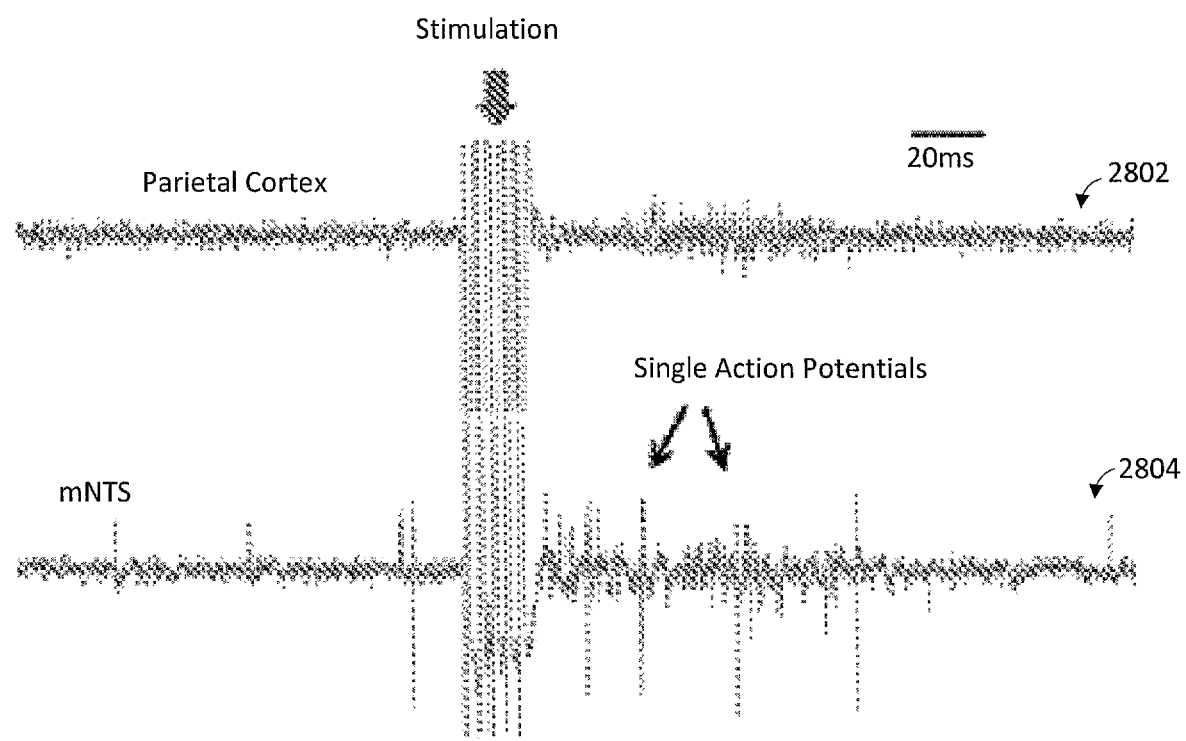
FIG. 28 shows plots of action potentials in a subject's autonomic nervous system and central nervous system during application of a particular micro burst signal.

FIGS. 27 and 28 illustrate results of acute electrophysiological experiments in rats under alpha-chloralose anesthesia. The experiments included assaying neuron activity in both the initial brain destination of vagal afferents (ipsilateral medial nucleus of the solitary tract—mNTS) as well as the parietal cortex. Extracellular action potentials were recorded using high impedance electrodes simultaneously in each location. Principal component analysis techniques identified an average of 3 neurons per site per experiment (n=IO rats). FIG. 27 illustrates graphs of action potentials in the parietal cortex and NTS when non-micro burst signals (current intensities of 0.25-0.75 mA, pulse width of 500 psec) at 30 Hz were applied. FIG. 28 illustrates graphs of action potentials in the parietal cortex and NTS when microburst signals microburst signals (5 pulses, pulse width of 500 psec at 250 Hz every 0.5 s) were applied.

With reference to trace 2704 of FIG. 27, non-microburst signals (current intensities of 0.25-0.75 mA, pulse width of 500 psec) at 30 Hz increased NTS neuronal activity significantly during the stimulation phase. Specifically, Activation of cervical vagus axons at 30 Hz evoked synchronous action potentials in the NTS at latencies averaging 16±1 ms. Following VNS using non-microburst signals, action potentials persisted in amplitude beyond the stimulus period. This persistent discharge likely represents a developing neuronal synchronization beginning at low amplitude (e.g., a few neurons) and gradually increasing in amplitude (e.g., more neurons). This suggests recruitment of additional NTS neurons that were inactive during baseline unstimulated conditions. In contrast, with reference to trace 2702 of FIG. 27, parietal cortex induced changes in activity were not detected. Thus, non-microburst signals at 30 Hz effectively synchronized and potentiated the amplitude of the neuronal activity in the NTS without causing significant changes in cortical activity.

With reference to trace 2804 of FIG. 28, application of the micro burst signals (5 pulses, pulse width of 500 µsec at 250 Hz every 0.5 s) evoked single action potentials in the NTS with every shock (0.25-0.75 mA) with latencies ranging from 8-50 ms. The latencies suggested activation of myelinated A,B-fibers and unmyelinated C-fibers, respectively. With reference to trace 2802 of FIG. 28, VNS using microburst signals also activated short latency action potentials in the parietal cortex with latencies ranging from 20-50 ms. Spontaneous cortical activity decreased significantly during the non-stimulating phase of microburst VNS from 6.6±3.1 Hz to 1.6±0.3 Hz. Thus, microburst signals effectively facilitated short latency neuronal responses in both the NTS and the parietal cortex. Consequently, the cortical activity significantly decreased during the unstimulated periods. Since the parietal cortex receives direct projections from limbic structures, the data showed that microburst VNS effectively recruited long lasting activation of the central neuroaxis. Non-microburst signals effectively increased synchrony between the subject's NTS and cortex.

Although the description above contains many specificities, these specificities are utilized to illustrate some of the exemplary embodiments of this disclosure and should not be construed as limiting the scope of the disclosure. The scope of this disclosure should be determined by the claims and their legal equivalents. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. § 112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising computer readable storage device, or machine-readable media for carrying, or having machine-executable instructions or data structures stored thereon. Such machine readable media can be any available media which can be accessed by a general purpose or special purpose computer or other machine with a processor. By way of example, such machine readable media can comprise RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multiprocessor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations and/or equipment for receiving manual inputs.

The foregoing descriptions of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A method comprising:
applying, by an implantable medical device (IMD), stimulation to a cranial nerve of a patient responsive to a determination that a level of synchrony between neural activity of one or more regions of an autonomic nervous system of the patient and one or more regions of a central nervous system of the patient falls below a first threshold; and
discontinuing the application of stimulation by the IMD when the level of synchrony exceeds a second threshold.

2. The method of claim 1, wherein the first threshold corresponds to a level of synchrony indicative of the onset of a seizure.

3. The method of claim 1, wherein the second threshold corresponds to a level of synchrony indicative of a non-seizure state.

4. The method of claim 1, wherein the first threshold and the second threshold correspond to a rate of change of the level of synchrony.

5. The method of claim 1, wherein the stimulation is applied in a first stimulation mode, the method further comprising applying, by the IMD, stimulation to the cranial nerve of the patient in a second stimulation mode in response to discontinuing the application of stimulation in the first stimulation mode.

6. The method of claim 5, wherein the first stimulation mode comprises microburst stimulation and the second stimulation mode comprises non-microburst stimulation.

7. The method of claim 5, wherein the first stimulation mode comprises non-microburst stimulation and the second stimulation mode comprises microburst stimulation.

8. The method of claim 1, further comprising determining, based on body parameter data collected by one or more sensors positioned on the patient, a first measurement indicative of the level of synchrony.

9. An implantable medical device (IMD) comprising:
a processor; and
a memory device having instructions stored thereon that, when executed by the processor, causes the processor to perform operations comprising:
applying, by one or more electrodes, stimulation to a cranial nerve of a patient responsive to a determination that a level of synchrony between neural activity of one or more regions of an autonomic nervous system of the patient and one or more regions of a central nervous system of the patient falls below a first threshold; and
discontinuing the application of stimulation when the level of synchrony exceeds a second threshold.

10. The IMD of claim 9, wherein the first threshold corresponds to a level of synchrony indicative of the onset of a seizure.

11. The IMD of claim 9, wherein the second threshold corresponds to a level of synchrony indicative of a non-seizure state.

12. The IMD of claim 9, wherein the first threshold and the second threshold correspond to a rate of change of the level of synchrony.

13. The IMD of claim 9, wherein the stimulation is applied in a first stimulation mode, the operations further comprising applying, by the one or more electrodes, stimulation to the cranial nerve of the patient in a second stimulation mode in response to discontinuing the application of stimulation in the first stimulation mode.

14. The IMD of claim 13, wherein the first stimulation mode comprises microburst stimulation and the second stimulation mode comprises non-microburst stimulation.

15. The IMD of claim 13, wherein the first stimulation mode comprises non-microburst stimulation and the second stimulation mode comprises microburst stimulation.

16. The IMD of claim 9, the operations further comprising determining, based on body parameter data collected by one or more sensors positioned on the patient, a first measurement indicative of the level of synchrony.

17. A computer-readable storage medium storing instructions thereon that, when executed by a processor of an implantable medical device (IMD), cause the IMD to:
apply stimulation to a cranial nerve of a patient responsive to a determination that a level of synchrony between neural activity of one or more regions of an autonomic nervous system of the patient and one or more regions of a central nervous system of the patient falls below a first threshold; and
discontinue the application of stimulation when the level of synchrony exceeds a second threshold.

18. The computer-readable storage medium of claim 17, wherein the first threshold corresponds to a level of synchrony indicative of the onset of a seizure and wherein the second threshold corresponds to a level of synchrony indicative of a non-seizure state.

19. The computer-readable storage medium of claim 17, wherein the first threshold and the second threshold correspond to a rate of change of the level of synchrony.

20. The computer-readable storage medium of claim 17, wherein the stimulation is applied in a first stimulation mode, the instructions further causing the IMD to apply stimulation to the cranial nerve of the patient in a second stimulation mode in response to discontinuing the application of stimulation in the first stimulation mode.

* * * * *